United States Patent [19]
Bandman et al.

[11] Patent Number: 5,871,965
[45] Date of Patent: Feb. 16, 1999

[54] GUANYLATE BINDING PROTEINS

[75] Inventors: Olga Bandman, Mountain View; Janice Au-Young, Berkeley; Jennifer L. Hillman, San Jose, all of Calif.

[73] Assignee: Incyte Pharmaceuticals, Inc., Palo Alto, Calif.

[21] Appl. No.: 736,770

[22] Filed: Oct. 25, 1996

[51] Int. Cl.$^6$ .............................. C07H 21/04; C12N 1/70; C12N 15/63

[52] U.S. Cl. .................. 435/69.1; 435/320.1; 435/252.1; 536/23.2

[58] Field of Search ........................ 536/23.2; 435/320.1, 435/252.1, 69.1

[56] References Cited

PUBLICATIONS

EMBL Sequence Database, Heidelberg, DE., Accession NR. AA075671, Hillier, L., et al., "Clone 545038 Similar to GB:M55543 Interferon–Induced Guanylate–Binding Proteing (Human)", XP002057290 Oct. 9, 1996.

Cheng, Y.E., et al., "Affinity Purification of an Interferon--induced Human Guanylate–binding Protein and Its Characterization," *The Journal of Biological Chemistry*, 260(29) :15834–15839 (1985).

Hamm, H.E., et al., "Site of G Protein Binding to Rhodopsin Mapped with Synthetic Peptides from the α Subunit," *Science*, 241:832–834 (1988).

*The Pharmacological Basis of Therapeutics*, 50:1211–1215 (1996).

Wynn, T.A., et al., "Identification and Characterization of a New Gene Family Induced During Macrophage Activation" *J. Immunol.*, 147:4384–4392 (1991).

Cheng, Y.S.E., et al., "Interferon–Induced Guanylate–Binding Proteins Lack an N(T)KXD Consensus Motif and Bind GMP in Addition to GDP and GTP" *Mol. Cell. Biol.*, 11:4717–4725 (1991).

Schwemmle, M., et al., "The Interferon–induced 67–kDa Guanylate–binding Protein (hGBP1) Is a GTPase That Converts GTP to GMP" *J. Biol. Chem.*, 269:11299–11305 (1994).

Neun, R., et al., "GTPase properties of the interferon–induced human guanylate–binding protein 2" *FEBS Letters*, 390:69–72 (1996).

Vestal, D.J., et al., "Rat p67 GBP is Induced by Interferon–γ and Isoprenoid–Modified in Macrophages" *Biochem. Biophys. Res. Commun.*, 224:528–534 (1996).

*Primary Examiner*—Thomas M. Cunningham
*Assistant Examiner*—Martha Lubet
*Attorney, Agent, or Firm*—Lucy J. Billings; Leanne C. Price; Incyte Pharmaceuticals, Inc.

[57] ABSTRACT

The present invention provides two human guanylate binding proteins (designated collectively as HGBP) and polynucleotides which identify and encode HGBP. The invention also provides genetically engineered expression vectors and host cells comprising the nucleic acid sequences encoding HGBP and a method for producing HGBP. The invention also provides for use of HGBP and agonists, antibodies, or antagonists specifically binding HGBP, in the prevention and treatment of diseases associated with expression of HGBP. Additionally, the invention provides for the use of antisense molecules to polynucleotides encoding HGBP for the treatment of diseases associated with the expression of HGBP. The invention also provides diagnostic assays which utilize the polynucleotide, or fragments or the complement thereof, and antibodies specifically binding HGBP.

8 Claims, 14 Drawing Sheets

```
                11              20              29              38              47              56
5' AAC ATC CTA GAC ATG GCT TTA GAG ATC CAC ATG TCA GAC CCC ATG TGC CTC ATC
                    M   A   L   E   I   H   M   S   D   P   M   C   L   I 65              74              83              92              101             110
GAG AAC TTT AAT GAG CAG CTG AAG GTT AAT CAG GAA GCT TTG GAG ATC CTG TCT
E   N   F   N   E   Q   L   K   V   N   Q   E   A   L   E   I   L   S 119             128             137             146             155             164
GCC ATT ACG CAA CCT GTA GTT GTG GTA GCG ATT GTG GGC CTC TAT CGC ACT GGC
A   I   T   Q   P   V   V   V   V   A   I   V   G   L   Y   R   T   G 173             182             191             200             209             218
AAA TCC TAC CTG ATG AAC AAG CTG GCT GGG AAG AAC AAG GGC TTC TCT GTT GCA
K   S   Y   L   M   N   K   L   A   G   K   N   K   G   F   S   V   A 227             236             245             254             263             272
TCT ACG GTG CAG TCT CAC ACC AAG GGA ATY TGG ATR TGG TGT GTG CCT CAT CCC
S   T   V   Q   S   H   T   K   G   I   W   X   W   C   V   P   H   P 281             290             299             308             317             326
AAG AAG CCA GAA CAC ACC CTA GTT CTG CTC GAC ACT GAG GGC CTG GGA GAT ATA
K   K   P   E   H   T   L   V   L   L   D   T   E   G   L   G   D   I 335             344             353             362             371             380
GAG AAG GGT GAC AAT GAG AAT GAC TCC TGG ATC TTT GCC TTG GCC ATC CTC CTG
E   K   G   D   N   E   N   D   S   W   I   F   A   L   A   I   L   L 389             398             407             416             425             434
AGC AGC ACC TTC GTG TAC AAT AGC ATA GGA ACC ATC AAC CAG CAG GCT ATG GAC
S   S   T   F   V   Y   N   S   I   G   T   I   N   Q   Q   A   M   D 443             452             461             470             479             488
CAA CTT CAC TAT GTG ACA GAG CTG ACA GAT CGA ATC AAG GCA AAC TCC TCA CCT
Q   L   H   Y   V   T   E   L   T   D   R   I   K   A   N   S   S   P 497             506             515             524             533             542
GGT AAC AAT TCT GTA GAC GAC TCA GCT GAC TTT GTG AGC TTT TTT CCA GCA TTT
G   N   N   S   V   D   D   S   A   D   F   V   S   F   F   P   A   F 551             560             569             578             587             596
GTG TGG ACT CTC AGA GAT TTC ACC CTG GAA CTG GAA GTA GAT GGA GAA CCC ATC
V   W   T   L   R   D   F   T   L   E   L   E   V   D   G   E   P   I 605             614             623             632             641             650
ACT GCT GAT GAC TAC TTG GAG CTT TCG CTA AAG CTA AGA AAA GGT ACT GAT AAG
T   A   D   D   Y   L   E   L   S   L   K   L   R   K   G   T   D   K 659             668             677             686             695             704
AAA AGT AAA AGC TTT AAT GAT CCT CGG TTG TGC ATC CGA AAG TTC TTN CCC AAG
K   S   K   S   F   N   D   P   R   L   C   I   R   K   F   X   P   K
```

FIGURE 1A

```
         713           722           731           740           749           758
AGG AAG TNC TTC GTC TTN GAT TGG CCC GNT NCT AAG AAG TAC CTT NCT NAC CTA
 R   K   X   F   V   X   D   W   P   X   X   K   K   Y   L   X   X   L 767           776           785           794           803           812
GAG CAG CTA AAG GAG GAA GAG CTG AAC CCT GAT TTC ATA GAA CAA GTT GCA GAA
 E   Q   L   K   E   E   E   L   N   P   D   F   I   E   Q   V   A   E 821           830           839           848           857           866
TTT TGT TCC TAC ATN CTC AGC CAT TCC AAT GTA CTA AGA CTC TTT CAG GTG GCA
 F   C   S   Y   X   L   S   H   S   N   V   L   R   L   F   Q   V   A 875           884           893           902           911           920
TTG CAG GTC AAT GGG CCT CGT CTA GAG AGC CTG GTG CTG ACC TAC GTC AAT GCC
 L   Q   V   N   G   P   R   L   E   S   L   V   L   T   Y   V   N   A 929           938           947           956           965           974
ATC GGC AGT GGG GAT CTA CCC TGC ATG GAG AAC GCA GTC CTG GCC TTG GCC CAG
 I   G   S   G   D   L   P   C   M   E   N   A   V   L   A   L   A   Q 983           992          1001          1010          1019          1028
ATA GAG AAC TCA GCY GCA GTG SAA AAG GCT ATT GCC CAC TAT GAA CAG YAG ATG
 I   E   N   S   A   A   V   X   K   A   I   A   H   Y   E   Q   X   M 1037          1046          1055          1064          1073          1082
GGC CAG AAG GTG CAG CTG CCC ACR GAA ACC CTC CAG GAG CTG CTG GAC CTG CAC
 G   Q   K   V   Q   L   P   T   E   T   L   Q   E   L   L   D   L   H 1091          1100          1109          1118          1127          1136
AGG GAC AGT GAG AGA GAG GCC ATT GAA GTC TTC ATG AAG AAC TCT TTC AAG GAT
 R   D   S   E   R   E   A   I   E   V   F   M   K   N   S   F   K   D 1145          1154          1163          1172          1181          1190
GTG GAC CAA ATG TTC CAG AGG AAA TTA GGG GCC CAG TTG GAA GCA AGG CGA GAT
 V   D   Q   M   F   Q   R   K   L   G   A   Q   L   E   A   R   R   D 1199          1208          1217          1226          1235          1244
GAC TTT TGT AAG CAG ANT TCC AAA GCA TNA TCA GAT TGT TGC ATG GCT TTA CTT
 D   F   C   K   Q   X   S   K   A   X   S   D   C   C   M   A   L   L 1253          1262          1271          1280          1289          1298
CAG GAT ATA TTT GGC CCT TTA GAA GAA GAT GTC AAG CAG GGA ACA TTT TCT AAA
 Q   D   I   F   G   P   L   E   E   D   V   K   Q   G   T   F   S   K 1307          1316          1325          1334          1343          1352
CCA GGG GGT TAC CGT CTC TTT ACT CAG AAG CTG CAG GAG CTG AAG GAT AAG TAC
 P   G   G   Y   R   L   F   T   Q   K   L   Q   E   L   K   D   K   Y 1361          1370          1379          1388          1397          1406
TAC CAG GTG CCA AGG AAG GGG ATA CAG GCC AAA GAG GTG CTG AAA AAA TAT TTG
 Y   Q   V   P   R   K   G   I   Q   A   K   E   V   L   K   K   Y   L
```

FIGURE 1B

```
          1415            1424            1433            1442            1451            1460
GAG TCC AAG GAG GAT GTG GCT GAT GCA CTT CTA CAG ACT GAT CAG TCA CTC TCA
 E   S   K   E   D   V   A   D   A   L   L   Q   T   D   Q   S   L   S 1469            1478            1487            1496            1505            1514
GAA AAG GAA AAA GCG ATT GAA GTG GAA CGT ATA AAG GCT GAA TCT GCA GAA GCT
 E   K   E   K   A   I   E   V   E   R   I   K   A   E   S   A   E   A 1523            1532            1541            1550            1559            1568
GCA AAG AAA ATG TTG GAG GAA ATA CAA AAG AAG AAT GAG GAG ATG ATG GAC CAG
 A   K   K   M   L   E   E   I   Q   K   K   N   E   E   M   M   D   Q 1577            1586            1595            1604            1613            1622
AAA GAG AAG AGT TAT CAG GAA CAT GTG AAA CAA TTG ACT GAG AAG ATG GAG AGG
 K   E   K   S   Y   Q   E   H   V   K   Q   L   T   E   K   M   E   R 1631            1640            1649            1658            1667            1676
GAC AGG GCC CAG TTA ATG GAA GAG CAA GAG AAG ACC CTC ACT AGT AAA CTT CAG
 D   R   A   Q   L   M   E   E   Q   E   K   T   L   T   S   K   L   Q 1685            1694            1703            1712            1721            1730
GAA CAG GCC CGA GCA CTA AAG GAG AGA TGC CAA GGT GAA AGT ACC CAA CTT CAA

E   Q   A   R   A   L   K   E   R   C   Q   G   E   S   T   Q   L   Q 1739            1748            1757            1766            1775            1784
AAT GAG ATA CAA AAG CTA CAG AAG ACC CTG AAA AAA AAA ACC AAG AGA TAT ATG
 N   E   I   Q   K   L   Q   K   T   L   K   K   K   T   K   R   Y   M 1793            1802            1811            1820            1829            1838
TNG NAT AAG CCT AAA AGG ATC CTA AAA CCA ACC AGG AGC TTT TTC TGT CAT NCC
 X   X   K   P   K   R   I   L   K   P   T   R   S   F   F   C   H   X 1847            1856            1865            1874            1883            1892
TAA CCC CCA AGG GCN ATT AAC CTG GAA AAC CAA ATT TTT TAG GAA TTT TGG GAA 1901            1910            1919            1928            1937            1946
CCA AGG TGG TCC ACT TAT TAA TNT TGG ATT AAA TTA AAT TTT AGG ANT CCT TTG 1955            1964            1973            1982            1991            2000
CCA ATC CAT TAA ACC ACT TTA AAA AGG TTT TTA CCA AAG GGA ANC CAA TGG CCA 2009            2018            2027            2036
GTT TTC AAA TTG GGA TTC CCA AAA AAA TCC NAT NGG TT 3'
```

FIGURE 1C

```
                9              18              27              36              45              54
5' AAC TTG GTG CTG CGG GCA CTT TGG GTC CAC ACT GCC TTT ATG AGC TGT AAC ACT 63              72              81              90              99             108
   CAC TGG GAA TGT CTG CAG CTT CAC TCC TGA AGC CAG CGA GAC CAC GAA CCC ACC 117             126             135             144             153             162
   AGG AGG AAC AAA CAA CTC CAG ACG CGC AGC CTT AAG AGC TGT AAC ACT CAC CGC 171             180             189             198             207             216
   GAA GGT CTG CAG CTT CAC TCC TGA GCC AGC CAG ACC ACG AAC CCA CCA GAA GGA 225             234             243             252             261             270
   AGA AAC TCC AAA CAC ATC CGA ACA TCA GAA GTG AGC AAA CTC CTG ACA CGC CAC 279             288             297             306             315             324
   CTT TAA GAA CCG TGA CAC TCA ACG CTA GGG TCC GCG GCT TCA TTC TTG AAG TCA 333             342             351             360             369             378
   GTG AGA CCA AGA ACC CAC CAA TTC CGG ACA CGG CAA AGT AAC ATC CTA GAC ATG
                                                                                             M 387             396             405             414             423             432
   GCT TTA GAG ATC CAC ATG TCA GAC CCC ATG TGC CTC ATC GAG AAC TTT AAT GAG
   A   L   E   I   H   M   S   D   P   M   C   L   I   E   N   F   N   E 441             450             459             468             477             486
   CAG CTG AAG GTT AAT CAG GAA GCT TTG GAG ATC CTG TCT GCC ATT ACG CAA CCT
   Q   L   K   V   N   Q   E   A   L   E   I   L   S   A   I   T   Q   P 495             504             513             522             531             540
   GTA GTT GTG GTA GCG ATT GTG GGC CTC TAT CGC ACT GGC AAA TCC TAC CTG ATG
   V   V   V   V   A   I   V   G   L   Y   R   T   G   K   S   Y   L   M 549             558             567             576             585             594
   AAC AAG CTG GCT GGG AAG AAC AAG GGC TTC TCT GTT GCA TCT ACG GTG CAG TCT
   N   K   L   A   G   K   N   K   G   F   S   V   A   S   T   V   Q   S 603             612             621             630             639             648
   CAC ACC AAG GGA ATT TGG ATA TGG TGT GTG CCT CAT CCC AAC TGG CCA AAT CAC
   H   T   K   G   I   W   I   W   C   V   P   H   P   N   W   P   N   H
```

FIGURE 2A

```
          657              666              675              684              693              702
ACA TTA TTC TGC TTG ACA CCG AGG CCT GGG AGA TGT AAA GCT GAC AAC AAG AAT
 T   L   F   C   L   T   P   R   P   G   R   C   K   A   D   N   K   N 711              720              729              738              747              756
GAT ATC CAG ATC TTT GCA CTG GCA CTC TTA CTG AGC AGC ACT TTN GTG TAC AAT
 D   I   Q   I   F   A   L   A   L   L   L   S   S   T   X   V   Y   N 765              774              783              792              801              810
ACT GTG AAC AAA ATT GAT CAG GGT GCT ATC GAC CTA CTG CAC AAT GTG ACA GAA
 T   V   N   K   I   D   Q   G   A   I   D   L   L   H   N   V   T   E 819              828              837              846              855              864
CTG ACA GAT CTG CTC AAG GCA AGA AAC TCA CCC GAC CTT GAC AGG GTT GAA GAT
 L   T   D   L   L   K   A   R   N   S   P   D   L   D   R   V   E   D 873              882              891              900              909              918
CCT GCT GAC TCT GCG AGC TTC TTC CCA GAC TTA GTG TGG ACT CTG AAA GAT TTC
 P   A   D   S   A   S   F   F   P   D   L   V   W   T   L   K   D   F 927              936              945              954              963              972
TGC TTA GGC CTG GAA ATA GAT GGG CAA CTT GTC ACA CCA GAT GAA TAC CTG GAG
 C   L   G   L   E   I   D   G   Q   L   V   T   P   D   E   Y   L   E 981              990              999              1008             1017             1026
AAT TCC CTA AGG CCA AAG CAA GGT AGT GAT CAA AGA GTT CAA AAT TTC AAT TTG
 N   S   L   R   P   K   Q   G   S   D   Q   R   V   Q   N   F   N   L 1035             1044             1053             1062             1071             1080
ACC CCG TCT GTG GTA TAC AGR AGT TCT TTC CAA AAA AAG GAA TGG TTT ATC TTT
 T   P   S   V   V   Y   R   S   S   F   Q   K   K   E   W   F   I   F 1089             1098             1107             1116             1125             1134
GAN TTA CCT GCT CAC CAA AAA AAG CTT GCC CAA CTT GAA ACA CTG CCT GAT GAT
 X   L   P   A   H   Q   K   K   L   A   Q   L   E   T   L   P   D   D 1143             1152             1161             1170             1179             1188
GAG CTA GAG CCT GAA TTT GTG CAA CAA GTG ACA GAA TTT TGT TCC TAC ATC TTT
 E   L   E   P   E   F   V   Q   Q   V   T   E   F   C   S   Y   I   F 1197             1206             1215             1224             1233             1242
AGC CAT TCA ATG ACC AAG ACT CTT CCA GGT GGC ATG CAG GTC AAT GGG CCT CGT
 S   H   S   M   T   K   T   L   P   G   G   M   Q   V   N   G   P   R 1251             1260             1269             1278             1287             1296
CTA GAG AGC CTG GTG CTG ACC TAC GTC AAT GCC ATC AGC AGT GGG GAT CTG CCT
 L   E   S   L   V   L   T   Y   V   N   A   I   S   S   G   D   L   P 1305             1314             1323             1332             1341             1350
TGC ATG GAG AAC GCA GTC CTG GCC TTG GCC CAG AGA GAG AAC TCA GCT GCA GTG
 C   M   E   N   A   V   L   A   L   A   Q   R   E   N   S   A   A   V
```

FIGURE 2B

```
       1359           1368           1377           1386           1395           1404
CAA AAG GCT ATT GCC CAC TAT GAC CAG CAG ATG GGC CAG AAG GTG CAG CTG CCC
 Q   K   A   I   A   H   Y   D   Q   Q   M   G   Q   K   V   Q   L   P 1413           1422           1431           1440           1449           1458
ACG GAA ACC CTC CAG GAG CTG CTG GAC CTG CAC AGG GAC AGT GAG AGA GAG GCC
 T   E   T   L   Q   E   L   L   D   L   H   R   D   S   E   R   E   A 1467           1476           1485           1494           1503           1512
ATT GAA GTC TTC ATG AAG AAC TCT TTC AAG GAT GTA GAC CAA AGT TTC CAG AAA
 I   E   V   F   M   K   N   S   F   K   D   V   D   Q   S   F   Q   K 1521           1530           1539           1548           1557           1566
GAA TTG GAG ACT CTA CTA GAT GCA AAA CAG AAT GAC ATT TGT AAA CGG AAC CTG
 E   L   E   T   L   L   D   A   K   Q   N   D   I   C   K   R   N   L 1575           1584           1593           1602           1611           1620
GAA GCA TCC TCG GAT TAT TGC TCG GCT TTA CTT AAG GAT ATT TTT GGT CCT CTA
 E   A   S   S   D   Y   C   S   A   L   L   K   D   I   F   G   P   L 1629           1638           1647           1656           1665           1674
GAA GAA GCA GTG AAG CAG GGA ATT TAT TCT AAG CCA GGA GGC CAT AAT CTC TTC
 E   E   A   V   K   Q   G   I   Y   S   K   P   G   G   H   N   L   F 1683           1692           1701           1710           1719           1728
ATT CAG AAA ACA GAA GAA CTG AAG GCA AAG TAC TAT CGG GAG CCT CGG AAA GGA
 I   Q   K   T   E   E   L   K   A   K   Y   Y   R   E   P   R   K   G 1737           1746           1755           1764           1773           1782
ATA CAG GCT GAA GAA GTT CTG CAG AAA TAT TTA AAG TCC AAG GAG TCT GTG AGT
 I   Q   A   E   E   V   L   Q   K   Y   L   K   S   K   E   S   V   S 1791           1800           1809           1818           1827           1836
CAT GCA ATA TTA CAG ACT GAC CAG GCT CTC ACA GAG ACG GAA AAA AAG AAG AAA
 H   A   I   L   Q   T   D   Q   A   L   T   E   T   E   K   K   K   K 1845           1854           1863           1872           1881           1890
GAG GCA CAA GTG AAA GCA GAA GCT GAA AAG GCT GAA GCG CAA AGG TTG GCG GCG
 E   A   Q   V   K   A   E   A   E   K   A   E   A   Q   R   L   A   A 1899           1908           1917           1926           1935           1944
ATT CAA AGG CAG AAC GAG CAA ATG ATG CAG GAG AGG GAG AGA CTC CAT CAG GAA
 I   Q   R   Q   N   E   Q   M   M   Q   E   R   E   R   L   H   Q   E 1953           1962           1971           1980           1989           1998
CAA GTG AGA CAA ATG GAG ATA GCC AAA CAA AAT TGG CTG GCA GAG CAA CAG AAA
 Q   V   R   Q   M   E   I   A   K   Q   N   W   L   A   E   Q   Q   K
```

FIGURE 2C

```
           2007            2016            2025            2034            2043            2052
ATG CAG GAA CAA CAG ATG CAG GAA CAG GCT GCA CAG TCA GCA CAA CAT TCC AAG
 M   Q   E   Q   Q   M   Q   E   Q   A   A   Q   S   A   Q   H   S   K 2061            2070            2079            2088            2097            2106
CTC AAA ATA GAG GCC TTC TCA GTG AGY TCC AGC ACG SCC AGA GGA CTG TTA ATA
 L   K   I   E   A   F   S   V   S   S   S   T   X   R   G   L   L   I 2115            2124            2133            2142            2151            2160
ACG ATG ATC CAT GTG TTT TAC TCT AAA GTG CTA AAT ATG GGA GTT TCC TTT TTT
 T   M   I   H   V   F   Y   S   K   V   L   N   M   G   V   S   F   F 2169            2178            2187            2196            2205            2214
TAC TCT TTG TCA CTG ATG ACA CAA CAG AAA AGA AAC TGT AGA CCT TGG GAC AAT
 Y   S   L   S   L   M   T   Q   Q   K   R   N   C   R   P   W   D   N 2223            2232            2241            2250            2259            2268
CAA CAT TTA AAT AAA CTT TAT AAT TAT TTT TTC AAA CTT TCA TAT AGA GTT ATA
 Q   H   L   N   K   L   Y   N   Y   F   F   K   L   S   Y   R   V   I 2277            2286            2295            2304            2313            2322
AGG TTA TGA TGC TGG TAT CTG GTA AAA TGT ACA TCC CAG TAG TCC AAT AGT TTA
 R   L 2331            2340            2349            2358            2367            2376
AAT GTT TAT TGC TTC CTT TAA GNG RTT ATA AAT TGT ATA AGG GAC ATT GTA TCA

CTG CC 3'
```

FIGURE 2D

| Library | Lib Description | Abun | Pct Abun |
|---|---|---|---|
| TMLR2DT01 | lymphocytes (non-adher PBMNC), M/F, 24-hr MLR | 3 | 0.0632 |
| MPHGLPT02 | macrophages (adher PBMNC), M/F, treated LPS | 1 | 0.0492 |
| MMLR1DT01 | macrophages (adher PBMNC), M/F, 24-hr MLR | 2 | 0.0471 |
| FIBRNOT01 | WI38 lung fibroblast cell line, fetal F | 1 | 0.0468 |
| KERANOT01 | keratinocytes, neonatal M | 2 | 0.0455 |
| LVENNOT01 | heart, left ventricle, 51 F | 1 | 0.0449 |
| THP1PLB02 | THP-1 promonocyte cell line, treated PMA, LPS | 1 | 0.0406 |
| OVARNOT03 | ovary, 43 F, match to OVARTUT01 | 1 | 0.0386 |
| NEUTFMT01 | granulocytes, periph blood, M/F, treated fMLP | 2 | 0.0349 |
| NEUTLPT01 | granulocytes, periph blood, M/F, treated LPS | 2 | 0.0335 |
| TBLYNOT01 | T-B lymphoblast cell line, leukemia | 1 | 0.0325 |
| THYRNOT02 | thyroid, hyperthyroidism, 16 F | 1 | 0.0302 |
| STOMNOT01 | stomach, 55 M | 1 | 0.0300 |
| BRSTTUT02 | breast tumor, 54 F, match to BRSTNOT03 | 1 | 0.0297 |
| SYNORAT05 | synovium, knee, rheumatoid, 62 F | 1 | 0.0286 |
| TMLR3DT02 | lymphocytes (non-adher PBMNC), M/F, 72-hr MLR | 1 | 0.0244 |
| SYNORAB01 | synovium, hip, rheumatoid, 68 F | 1 | 0.0194 |
| MMLR2DT01 | macrophages (adher PBMNC), M/F, 48-hr MLR | 1 | 0.0177 |
| BRAITUT02 | brain tumor, metastasis, 58 M | 1 | 0.0169 |
| UTRSNOT02 | uterus, 34 F | 1 | 0.0166 |
| BRSTNOT02 | breast, 55 F, match to BRSTTUT01 | 1 | 0.0158 |
| NEUTGMT01 | granulocytes, periph blood, M/F, treated GM-CSF | 1 | 0.0156 |
| CORPNOT02 | brain, corpus callosum, Alzheimer's, 74 M | 1 | 0.0152 |
| BRSTTUT01 | breast tumor, 55 F, match to BRSTNOT02 | 1 | 0.0150 |
| BRSTTUT03 | breast tumor, 58 F, match to BRSTNOT05 | 1 | 0.0148 |
| BRSTNOT03 | breast, 54 F, match to BRSTTUT02 | 1 | 0.0146 |
| UCMCL5T01 | mononuclear cells, treated IL-5 | 1 | 0.0125 |

The Northern returned a total of 27 results.

FIGURE 3

| Library | Lib Description | Abun | Pct Abun |
|---|---|---|---|
| MMLR1DT01 | macrophages (adher PBMNC), M/F, 24-hr MLR | 7 | 0.1651 |
| MMLR3DT01 | macrophages (adher PBMNC), M/F, 72-hr MLR | 4 | 0.1324 |
| MMLR2DT01 | macrophages (adher PBMNC), M/F, 48-hr MLR | 7 | 0.1239 |
| TESTNOT04 | testis, 37 M | 1 | 0.1072 |
| MPHGLPT02 | macrophages (adher PBMNC), M/F, treated L | 2 | 0.0985 |
| TMLR3DT02 | lymphocytes (non-adher PBMNC), M/F, 72-hr | 4 | 0.0979 |
| TMLR2DT01 | lymphocytes (non-adher PBMNC), M/F, 24-h | 4 | 0.0843 |
| HEARNOT01 | heart, 56 M | 1 | 0.0707 |
| PROSTUT03 | prostate tumor, 67 M, match to PROSNOT( | 2 | 0.0703 |
| NEUTFMT01 | granulocytes, periph blood, M/F, treat | 4 | 0.0698 |
| TMLR3DT01 | lymphocytes (non-adher PBMNC), M, 96-' | 3 | 0.0686 |
| NEUTGMT01 | granulocytes, periph blood, M/F, tre | 4 | 0.0625 |
| PANCTUT02 | pancreatic tumor, carcinoma, 45 F | 2 | 0.0577 |
| NEUTLPT01 | granulocytes, periph blood, M/F, tr | 3 | 0.0503 |
| COLNCRT01 | colon, Crohn's, 40 M, match to COL | 1 | 0.0467 |
| THYRNOT01 | thyroid, 64 F | 2 | 0.0455 |
| BRSTTUT01 | breast tumor, 55 F, match to BRST | 3 | 0.0452 |
| PITUNOT01 | pituitary, 16-70 M/F | 1 | 0.0423 |
| THP1PLB02 | THP-1 promonocyte cell line, tre | 1 | 0.0406 |
| MUSCNOT02 | muscle, psoas, 12 M | 1 | 0.0381 |
| LUNGTUT02 | lung tumor, metastasis, 79 M, | 2 | 0.0377 |
| HMC1NOT01 | HMC-1 mast cell line, 52 F | 1 | 0.0333 |
| BRSTNOT07 | breast, 43 F | 1 | 0.0307 |
| COLNNOT11 | colon, 60 M | 1 | 0.0307 |
| STOMNOT01 | stomach, 55 M | 1 | 0.0300 |
| BRSTTUT02 | breast tumor, 54 F, match to BRSTNOT03 | 1 | 0.0297 |
| SYNORAT05 | synovium, knee, rheumatoid, 62 F | 1 | 0.0286 |
| BMARNOT02 | bone marrow, 16-70 M/F | 1 | 0.0269 |
| PANCTUT01 | pancreatic tumor, 65 F, match to PANCNOT08 | 1 | 0.0257 |
| COLNNOT01 | colon, 75 M, match to COLNTUT02 | 1 | 0.0213 |
| THYMNOT02 | thymus, 3 M | 1 | 0.0193 |
| ADENINB01 | adenoid, inflamed, 3y | 1 | 0.0190 |
| PLACNOT02 | placenta, fetal F | 1 | 0.0167 |
| UTRSNOT02 | uterus, 34 F | 1 | 0.0166 |
| BRSTNOT05 | breast, 58 F, match to BRSTTUT03 | 1 | 0.0154 |
| CORPNOT02 | brain, corpus callosum, Alzheimer's, 74 M | 1 | 0.0152 |
| LUNGAST01 | lung, asthma, 17 M | 1 | 0.0150 |

The Northern returned a total of 37 results.

FIGURE 4

| | | |
|---|---|---|
| 1 | M A L E I H M S D P M C L I E N F N E Q L K V N Q E A L E I | SEQ ID NO-1 |
| 1 | M A P E I N L P G P M S L I D N T K G Q L V V N P E A L K I | GI 829177 |
| 1 | M A L E I H M S D P M C L I E N F N E Q L K V N Q E A L E I | SEQ ID NO-3 |
| 1 | M A S E I H M T G P M C L I E N T G R L M A N P E A L K I | GI 183002 |
| 31 | L S A I T Q P V V V V A I V G L Y R T G K S Y L M N K L A G | SEQ ID NO-1 |
| 31 | L S A I T Q P V V V V A I V G L Y R T G K S Y L M N K L A G | GI 829177 |
| 31 | L S A I T Q P V V V V A I V G L Y R T G K S Y L M N K L A G | SEQ ID NO-3 |
| 31 | L S A I T Q P M V V V A I V G L Y R T G K S Y L M N K L A G | GI 183002 |
| 61 | K N K G F S V A S T V Q S H T K G I W X W C V P H P K K P E | SEQ ID NO-1 |
| 61 | K N G F S L G S T V K S H T K G I W M W C V P H P K K P E | GI 829177 |
| 61 | K N K G F S V A S T V Q S H T K G I W I W C V P H P N W P N | SEQ ID NO-3 |
| 61 | K K K G F S L G S T V Q S H T K G I W M W C V P H P K K P G | GI 183002 |
| 91 | H T L V L L D T E G L G D I E K G D N E N D S W I F A L A I | SEQ ID NO-1 |
| 91 | H T L V L L D T E G L G D I E K G D N E N D S W I F A L A I | GI 829177 |
| 91 | H T L F C L T P R - - P G R C K A D N K N D I Q I F A L A L | SEQ ID NO-3 |
| 91 | H I L V L L D T E G L G D V E K G D N Q N D S W I F A L A V | GI 183002 |
| 121 | L L S S T F V Y N S I G T I N Q Q A M D Q L H Y V T E L T D | SEQ ID NO-1 |
| 121 | L L S S T F V Y N S M G T I N Q Q A M D Q L H Y V T E L T D | GI 829177 |
| 119 | L L S S T X V Y N T V N K I D Q G A I D L L H N V T E L T D | SEQ ID NO-3 |
| 121 | L L S S T F V Y N S I G T I N Q Q A M D Q L Y Y V T E L T H | GI 183002 |
| 151 | R I K A N S S P G N N S - - V D D S A D F V S F F P A F V W | SEQ ID NO-1 |
| 151 | R I K A N S S P G N N S - - V D D S A D F V S F F P A F V W | GI 829177 |
| 149 | L L K A R N S P D L D R - - V E D P A D S A S F F P D L V W | SEQ ID NO-3 |
| 151 | R I R S K S S P D E N E N E V E D S A D F V S F F P D F V W | GI 183002 |
| 179 | T L R D F T L E L E V D G E P I T A D D Y L E L S L K L R K | SEQ ID NO-1 |
| 179 | T L R D F T L E L E V D G E P I T A D D Y L E L S L K L R K | GI 829177 |
| 177 | T L K D F C L G L E I D G Q L V T P D E Y L E N S L R P K Q | SEQ ID NO-3 |
| 181 | T L R D F S L D L E A D G Q P L T P D E Y L T Y S L K L K K | GI 183002 |
| 209 | G T D K K S K S F N D - P R L C I R K F X P K R K X F V X D | SEQ ID NO-1 |
| 209 | G T D K K S K S F N D - P R L C I R K F F P K R K C F V F D | GI 829177 |
| 207 | G S D Q R V Q N F N L T P S V V Y R S S F Q K K E W F I F X | SEQ ID NO-3 |
| 211 | G T S Q K D E T F N L - P R L C I R K F F P K K K C F V F D | GI 183002 |
| 238 | W P X X K K Y L X X L E Q L K E E E L N P D F I E Q V A E F | SEQ ID NO-1 |
| 238 | W P A P K K Y L A H L E Q L K E E E L N P D F I E Q V A E F | GI 829177 |
| 237 | L P A H Q K K L A Q L E T L P D D E L E P E F V Q Q V T E F | SEQ ID NO-3 |
| 240 | R P V H R R K L A Q L E K L Q D E E L D P E F V Q Q V A D F | GI 183002 |
| 268 | C S Y X L S H S N V L R L F Q V A L Q V N G P R L E S L V L | SEQ ID NO-1 |
| 268 | C S Y I L S H S N V - K T L S G G I A V N G P R L E S L V L | GI 829177 |
| 267 | C S Y I F S H S M T - K T L P G G M Q V N G P R L E S L V L | SEQ ID NO-3 |
| 270 | C S Y I F S N S K T - K T L S G G I Q V N G P R L E S L V L | GI 183002 |
| 298 | T Y V N A I G S G D L P C M E N A V L A L A Q I E N S A A V | SEQ ID NO-1 |
| 297 | T Y V N A I S S G D L P C M E N A V L A L A Q I E N S A A V | GI 829177 |
| 296 | T Y V N A I S S G D L P C M E N A V L A L A Q R E N S A A V | SEQ ID NO-3 |
| 299 | T Y V N A I S S G D L P C M E N A V L A L A Q I E N S A A V | GI 183002 |

FIGURE 5A

```
328 X K A I A H Y E Q X M G Q K V Q L P T E T L Q E L L D L H R    SEQ ID NO-1
327 E K A I A H Y E Q Q M G Q K V Q L P T E T L Q E L L D L H R    GI 829177
326 Q K A I A H Y D Q Q M G Q K V Q L P T E T L Q E L L D L H R    SEQ ID NO-3
329 Q K A I A H Y E Q Q M G Q K V Q L P T E S L Q E L L D L H R    GI 183002

358 D S E R E A I E V F M K N S F K D V D Q M F Q R K L G A Q L    SEQ ID NO-1
357 D S E R E A I E V F M K N S F K D V D Q M F Q R K L G A Q L    GI 829177
356 D S E R E A I E V F M K N S F K D V D Q S F Q K E L E T L L    SEQ ID NO-3
359 D S E R E A I E V F I R S S F K D V D H L F Q K E L A A Q L    GI 183002

388 E A R D D F C K Q X S K A X S D C C M A L L Q D I F G P L    SEQ ID NO-1
387 E A R R D D F C K Q N S K A S S D C C M A L L Q D I F G P L    GI 829177
386 D A K Q N D I C K R N L E A S S D Y C S A L L K D I F G P L    SEQ ID NO-3
389 E K K R D D F C K Q N Q E A S S D R C S G L L Q V I F S P L    GI 183002

418 E E D V K Q G T F S K P G G Y R L F T Q K L Q E L K D K Y Y    SEQ ID NO-1
417 E E D V K Q G T F S K P G G Y R L F T Q K L Q E L K N K Y Y    GI 829177
416 E E A V K Q G I Y S K P G G H N L F I Q K T E E L K A K Y Y    SEQ ID NO-3
419 E E E V K A G I Y S K P G G Y R L F V Q K L Q D L K K K Y Y    GI 183002

448 Q V P R K G I Q A K E V L K K Y L E S K E D V A D A L L Q T    SEQ ID NO-1
447 Q V P R K G I Q A K E V L K K Y L E S K E D V A D A L L Q T    GI 829177
446 R E P R K G I Q A E E V L Q K Y L K S K E S V S H A I L Q T    SEQ ID NO-3
449 E E P R K G I Q A E E I L Q T Y L K S K E S M T D A I L Q T    GI 183002

478 D Q S L S E K E K A I E V E R I K A E S A E A A K M L E E    SEQ ID NO-1
477 D Q S L S E K E K A I E V E R I K A E S A E A A K M L E E    GI 829177
476 D Q A L T E T E K K K K E A Q V K A E A E K A E A Q R L A A    SEQ ID NO-3
479 D Q T L T E K E K E I E V E R V K A E S A Q A S A K M L Q E    GI 183002

508 I Q K K N E E M M D Q K E K S Y Q E H V K Q L T E K M E R D    SEQ ID NO-1
507 I Q K K N E E M M E Q K E K S Y Q E H V K Q L T E K M E R D    GI 829177
506 L I Q R Q N E Q M M Q E R E R L H Q E Q V R Q - - - - M E I A    SEQ ID NO-3
509 M Q R K N E Q M M E Q K E R S Y Q E H L K Q L T E K M E N D    GI 183002

538 R A Q L M E E Q E K T L T S K L Q E Q A - - - - - - - R A L    SEQ ID NO-1
537 R A Q L M A E Q E K T L A L K L Q E Q E - - - - - - - R L L    GI 829177
532 K Q N W L A E Q Q K M Q E Q Q M Q E Q A A Q S A Q H S K L K    SEQ ID NO-3
539 R V Q L L K E Q E R T L A L K L Q E Q E - - - - - - - Q L L    GI 183002

561 K E R C Q G E S T Q L Q N E I Q K L Q K - - - - - - - - - -    SEQ ID NO-1
560 K E G F E N E S K R L Q K D I W D I Q - - - - - - - - - - -    GI 829177
562 I E A F S V S S T X R G L L I T M I H V F Y S K V L N M G    SEQ ID NO-3
562 K E G F Q K E S R I M K N E I Q D L Q T - - - - - - - - - -    GI 183002

581 - - - - - - T L K K K T K R Y M X X K P K R I L K P T R S    SEQ ID NO-1
579 - - - - - - - - - - - - - - M R S K S - - - L E P - - -    GI 829177
592 V S F F Y S L S L M T Q Q K R N C R P W D N Q H L N K L Y N    SEQ ID NO-3
582 - - - - - - K M R R R K A - - - - - - - - - - - - - - -    GI 183002

604 F F C H X                                                      SEQ ID NO-1
587 - I C N I - - - - - - L                                        GI 829177
622 Y F F K L S Y R V I R L                                        SEQ ID NO-3
589 - - C T I - - - - - - S                                        GI 183002
```

FIGURE 5B

GUANYLATE BINDING PROTEINS

FIELD OF THE INVENTION

This invention relates to nucleic acid and amino acid sequences of novel human guanylate binding proteins and to the use of these sequences in the diagnosis, prevention, and treatment of cancer, viral infections, inflammation, or conditions associated with impaired immunity.

BACKGROUND OF THE INVENTION

Interferons (IFNs) are members of a group of intercellular messenger proteins known as cytokines. γ-IFN, also known as type II IFN, is produced in T-cells and natural killer cells. Biosynthesis of γ-IFN is stimulated by antigens to which the organism has been sensitized. IFNs' immunomodulatory and anti-inflammatory actions are part of the body's natural defense against viruses and cancers. They exert these defenses by affecting the function of the immune system and by direct action on pathogens and cancer cells. IFNs mediate these multiple effects in part by inducing the synthesis of many cellular proteins. Some IFN induced (IFI) proteins are preferentially induced by γ-IFN.

The various IFI proteins possess anti-cancer, antiviral and immunomodulatory functions. For example, IFI proteins are known to inhibit viral functions such as cell penetration, uncoating, RNA and protein synthesis, assembly and release (cf Hardman J. G. et al. (1996) *The Pharmacological Basis of Therapeutics*, McGraw-Hill, New York, N.Y. pp 1211–1215). Furthermore, induction of major histocompatibility complex (MHC) proteins by γ-IFN can enhance an immune response enhancement.

The human macrophage cell line, RAW 264.7, responds to stimulation with γ-IFN plus lipopolysaccharide (LPS) by the development of cytolytic activity. Two closely homologous genes (76% identity in amino acid sequence) were found to be induced by γ-IFN stimulation of RAW 264.7 cells, but not induced in the non-tumoricidal line WEHI-3 (Wynn T. A. et al. (1991) J. Immunol. 147: 4384–4392). The protein products of these genes were found to selectively bind guanine mono, di, and tri phosphate (GMP, GDP, and GTP) and were therefore named guanylate-binding proteins 1 and 2 (GBP-1 and GBP-2; Cheng Y. E. et al. (1991) Mol. Cell. Biol. 11: 4717–4725). Sequence analysis revealed that the GBPs contain two of three highly conserved guanine-nucleotide-binding motifs GXXXXGKS(T) and DXXG, but lack the third, N(T)KXD. Despite the lack of this third binding motif, which was thought to be important for guanine specificity, GBPs interact with GTP but not with ATP or other nucleotides. Experimental evidence revealed that human GBP-1 is a GTPase, hydrolyzing GTP to GMP (Schwemmle M. et al. (1994) J. Biol. Chem. 269: 11299–11305). GDP does not appear to be a major substrate, inhibitor, or product of GBP-1 (Schwemmle et al., supra). Recently, human GBP-2 was found to hydrolyze GTP to GDP (Neun R. et al. (1996) FEBS Lett. 390: 69–72). Thus, although human GBP-1 and GBP-2 appear to have similar biological activities, they show differences in product specificity.

Indirect immunofluorescence analysis of both γ-IFN treated human cells and transfected mouse cells, using antibodies specific for human GBP-1, showed a staining pattern that suggested that GBP-1 was associated with the inner cell membrane (Schwemrle et al., supra). Additionally, in vitro assays showed that an isoprenylation motif, CaaX, at the C terminus of human GBP-1 does indeed function as a isoprenylation signal, allowing the addition of a 20-carbon molecule that serves to anchor the protein to a membrane (Schwemmle et al., supra). GBP-2 also contains the CaaX motif, thus both GBPs appear to be membrane-associated. A rat GBP was found to be prenylated in vivo (Vestal D. J. et al. (1996) Biochem. Biophys. Res. Commun. 224: 528–534). The rat GBP was found to be induced by both γ-IFN and LPS in cultured macrophages and microglia (Vestal et al. supra). LPS induction of human GBPs has not been reported. The expression patterns of human GBP-1 and GBP-2 are distinct, but both appear to be restricted to γ-IFN induced macrophages and fibroblasts. Although the specific function of GBPs is not known, expression pattern and aspects of their amino acid sequence suggest that GBPs are important agents in the development of tumoricidal macrophages (supra). GBPs have also been characterized as potential intracellular mediators of γ-IFN induced antiviral effects (Chen et al., supra).

The discovery of polynucleotides encoding human guanylate-binding proteins produced by immune system cells, and the molecules themselves, presents the opportunity to investigate γ-IFN mediated anti-viral, anti-inflammatory, and anti-cancer activities. Discovery of molecules related to GBPs satisfies a need in the art by providing new diagnostic or therapeutic compositions useful in the diagnosis and treatment of cancer, viral infections, inflammation, or conditions associated with impaired immunity.

SUMMARY OF THE INVENTION

The present invention features novel guanylate binding proteins, hereinafter designated collectively as HGBP and individually as HGBPA and HGBPB, characterized as having similarity to interferon-induced guanylate binding proteins.

Accordingly, the invention features substantially purified HGBP, with amino acid sequences as shown in SEQ ID NO:1 and SEQ ID NO:3, having chemical homology to human GBPs.

One aspect of the invention features isolated and substantially purified polynucleotides that encode HGBP. In a particular aspect, the polynucleotide is the nucleotide sequence of SEQ ID NO:2 and SEQ ID NO:4.

The invention also relates to a polynucleotide sequence comprising the complement of SEQ ID NO:2 and SEQ ID NO:4 or variants thereof. In addition, the invention features polynucleotide sequences which hybridize under stringent conditions to SEQ ID NO:2 and SEQ ID NO:4.

The invention additionally features nucleic acid sequences encoding polypeptides, oligonucleotides, peptide nucleic acids (PNA), fragments, portions or antisense molecules thereof, and expression vectors and host cells comprising polynucleotides that encode HGBP. The present invention also features antibodies which bind specifically to HGBP, and pharmaceutical compositions comprising substantially purified HGBP. The invention also features the use of agonists and antagonists of HGBP.

BRIEF DESCRIPTION OF THE FIGURES

FIGS. 1A, 1B, and 1C show the amino acid sequence (SEQ ID NO:1) and nucleic acid sequence (SEQ ID NO:2) of HGBPA. The alignment was produced using MACDNASIS PRO software (Hitachi Software Engineering Co., Ltd., San Bruno, Calif.).

FIGS. 2A, 2B, 2C, and 2D show the amino acid sequence (SEQ ID NO:3) and nucleic acid sequence (SEQ ID NO:4) of HGBPB.

FIG. 3 shows the northern analysis for SEQ ID NO:2. The northern analysis was produced electronically using LIFESEQ database (Incyte Pharmaceuticals, Inc., Palo Alto, Calif.).

FIG. 4 shows the northern analysis for SEQ ID NO:4.

FIGS. 5A and 5B show the amino acid sequence alignments among HGBPA (SEQ ID NO:1), human GBP-2 (GI 829177; SEQ ID NO:5), HGBPB (SEQ ID NO:3), and human GBP-1 (GI 183002; SEQ ID NO:6). The alignment was produced using the multisequence alignment program of DNASTART software (DNASTAR Inc, Madison Wis.).

DESCRIPTION OF THE INVENTION

Figure 6:
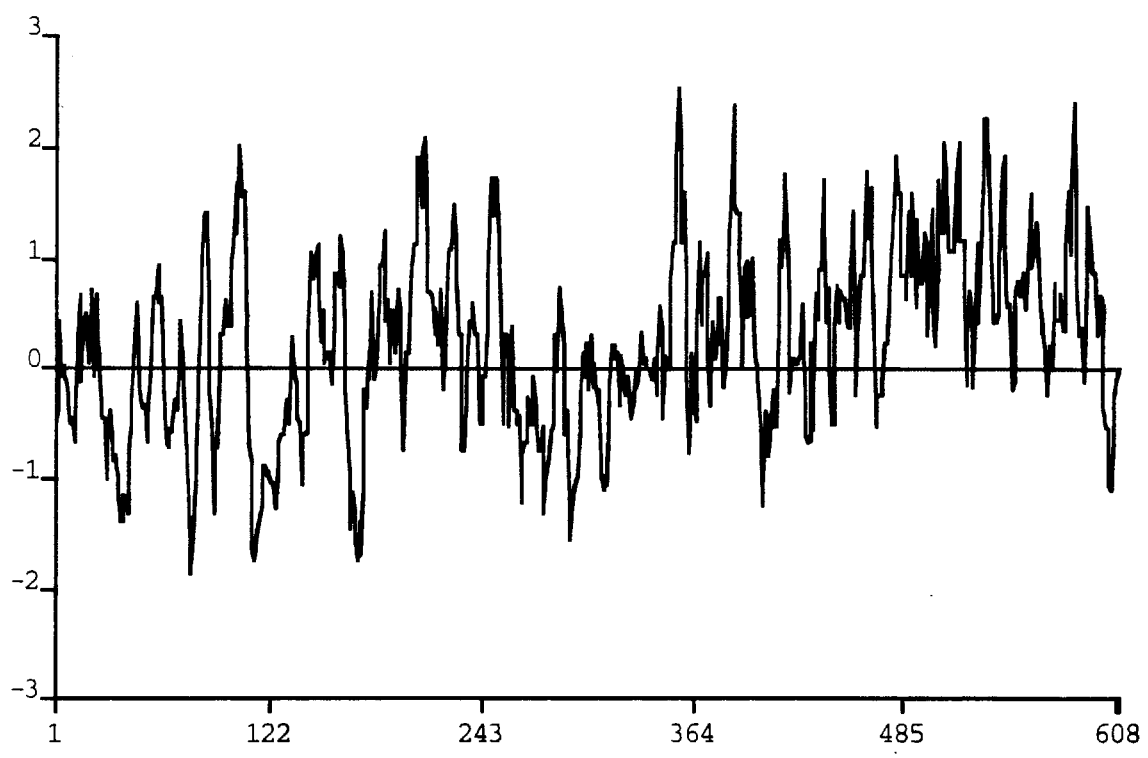
FIG. 6 shows the hydrophobicity plot (MACDNASIS PRO software) for HGBPA, SEQ ID NO:1; the positive X axis reflects amino acid position, and the negative Y axis reflects, hydrophobicity.

Before the present protein, nucleotide sequence, and methods are described, it is understood that this invention is not limited to the particular methodology, protocols, cell lines, vectors, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise.

Thus, for example, reference to "a host cell" includes a plurality of such host cells, reference to the "antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies which are reported in the publications which might be used in connection with the invention. Nothing herein is to be construed as an admission that the invention is not entitled to antedate such disclosure by virtue of prior invention.

DEFINITIONS

"Nucleic acid sequence" as used herein refers to an oligonucleotide, nucleotide, or polynucleotide, and fragments or portions thereof, and to DNA or RNA of genomic or synthetic origin which may be single- or double-stranded, and represent the sense or antisense strand. Similarly, "amino acid sequence" as used herein refers to an oligopeptide, peptide, polypeptide, or protein sequence and fragments or portions thereof, of a naturally occurring or synthetic molecule.

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule.

"Peptide nucleic acid", as used herein, refers to a molecule which comprises an oligomer to which an amino acid residue, such as lysine, and an amino group have been added. These small molecules, also designated anti-gene agents, stop transcript elongation by binding to their complementary strand of nucleic acid (Nielsen et al. (1993) Anticancer Drug Des. 8:53–63).

HGBP, as used herein, refers to the amino acid sequences of substantially purified HGBP obtained from any species, particularly mammalian, including bovine, ovine, porcine, murine, equine, and preferably human, from any source whether natural, synthetic, semi-synthetic, or recombinant.

"Consensus", as used herein, refers to a nucleic acid sequence which has been resequenced to resolve uncalled bases, or which has been extended using XL-PCR (Perkin Elmer, Norwalk, Conn.) in the 5' and/or the 3' direction and resequenced, or which has been assembled from the overlapping sequences of more than one Incyte clone using the GELVIEW Fragemet Assembly system (GCG, Madison, Wis.), or which has been both extended and assembled.

A "variant" of HGBP, as used herein, refers to an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Similar minor variations may also include amino acid deletions or insertions, or both. Guidance in determining which amino acid residues may be substituted, inserted, or deleted without abolishing biological or immunological activity may be found using computer programs well known in the art, for example, DNASTAR software.

A "deletion", as used herein, refers to a change in either amino acid or nucleotide sequence in which one or more amino acid or nucleotide residues, respectively, are absent.

An "insertion" or "addition", as used herein, refers to a change in an amino acid or nucleotide sequence resulting in the addition of one or more amino acid or nucleotide residues, respectively, as compared to the naturally occurring molecule.

A "substitution", as used herein, refers to the replacement of one or more amino acids or nucleotides by different amino acids or nucleotides, respectively.

The term "biologically active", as used herein, refers to a protein having structural, regulatory, or biochemical functions of a naturally occurring molecule. Likewise, "immunologically active" refers to the capability of the natural, recombinant, or synthetic HGBP, or any oligopeptide thereof, to induce a specific immune response in appropriate animals or cells and to bind with specific antibodies.

The term "agonist", as used herein, refers to a molecule which, when bound to HGBP, causes a change in HGBP which modulates the activity of HGBP. Agonists may include proteins, nucleic acids, carbohydrates, or any other molecules which bind to HGBP.

The terms "antagonist" or "inhibitor", as used herein, refer to a molecule which, when bound to HGBP, blocks the biological or immunological activity of HGBP. Antagonists and inhibitors may include proteins, nucleic acids, carbohydrates, or any other molecules which bind to HGBP.

The term "modulate", as used herein, refers to a change or an alteration in the biological activity of HGBP. Modulation may be an increase or a decrease in protein activity, a change in binding characteristics, or any other change in the biological, functional or immunological properties of HGBP.

The term "mimetic", as used herein, refers to a molecule, the structure of which is developed from knowledge of the structure of HGBP or portions thereof and, as such, is able to effect some or all of the actions of HGBP-like molecules.

The term "derivative", as used herein, refers to the chemical modification of a nucleic acid encoding HGBP or the encoded HGBP. Illustrative of such modifications would be replacement of hydrogen by an alkyl, acyl, or amino group. A nucleic acid derivative would encode a polypeptide which retains essential biological characteristics of the natural molecule.

The term "substantially purified", as used herein, refers to nucleic or amino acid sequences that are removed from their natural environment, isolated or separated, and are at least 60% free, preferably 75% free, and most preferably 90% free from other components with which they are naturally associated.

"Amplification" as used herein refers to the production of additional copies of a nucleic acid sequence and is generally carried out using polymerase chain reaction (PCR) technologies well known in the art (Dieffenbach, C. W. and G. S. Dveksler (1995) *PCR Primer, a Laboratory Manual*, Cold Spring Harbor Press, Plainview, N.Y.).

The term "hybridization", as used herein, refers to any process by which a strand of nucleic acid binds with a complementary strand through base pairing.

The term "hybridization complex", as used herein, refers to a complex formed between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0t$ or $R_0t$ analysis) or between one nucleic acid sequence present in solution and another nucleic acid sequence immobilized on a solid support (e.g., membranes, filters, chips, pins or glass slides to which cells have been fixed for in situ hybridization).

The terms "complementary" or "complementarity", as used herein, refer to the natural binding of polynucleotides under permissive salt and temperature conditions by base-pairing. For example, for the sequence "A-G-T" binds to the complementary sequence "T-C-A". Complementarity between two single-stranded molecules may be "partial", in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acids strands.

The term "homology", as used herein, refers to a degree of complementarity. There may be partial homology or complete homology (i.e., identity). A partially complementary sequence is one that at least partially inhibits an identical sequence from hybridizing to a target nucleic acid; it is referred to using the fulnctional term "substantially homologous." The inhibition of hybridization of the completely complementary sequence to the target sequence may be examined using a hybridization assay (Southern or northern blot, solution hybridization and the like) under conditions of low stringency. A substantially homologous sequence or probe will compete for and inhibit the binding (i.e., the hybridization) of a completely homologous sequence or probe to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity); in the absence of non-specific binding, the probe will not hybridize to the second non-complementary target sequence.

As known in the art, numerous equivalent conditions may be employed to comprise either low or high stringency conditions. Factors such as the length and nature (DNA, RNA, base composition) of the sequence, nature of the target (DNA, RNA, base composition, presence in solution or immobilization, etc.), and the concentration of the salts and other components (e.g., the presence or absence of formamide, dextran sulfate and/or polyethylene glycol) are considered and the hybridization solution may be varied to generate conditions of either low or high stringency different from, but equivalent to, the above listed conditions.

The term "stringent conditions", as used herein, is the "stringency" which occurs within a range from about Tm-5° C. (5° C. below the melting temperature (Tm) of the probe) to about 20° C. to 25° C. below Tm. As will be understood by those of skill in the art, the stringency of hybridization may be altered in order to identify or detect identical or related polynucleotide sequences.

The term "antisense", as used herein, refers to nucleotide sequences which are complementary to a specific DNA or RNA sequence. The term "antisense strand" is used in reference to a nucleic acid strand that is complementary to the "sense" strand. Antisense molecules may be produced by any method, including synthesis by ligating the gene(s) of interest in a reverse orientation to a viral promoter which permits the synthesis of a complementary strand. Once introduced into a cell, this transcribed strand combines with natural sequences produced by the cell to form duplexes. These duplexes then block either the further transcription or translation. In this manner, mutant phenotypes may be generated. The designation "negative" is sometimes used in reference to the antisense strand, and "positive" is sometimes used in reference to the sense strand.

The term "portion", as used herein, with regard to a protein (as in "a portion of a given protein") refers to fragments of that protein. The fragments may range in size from four amino acid residues to the entire amino acid sequence minus one amino acid. Thus, a protein "comprising at least a portion of the amino acid sequence of SEQ ID NO:1 or SEQ ID NO:3" encompasses the full-length human HGBP and fragments thereof.

"Transformation", as defined herein, describes a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the host cell being transformed and may include, but are not limited to, viral infection, electroporation, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

The term "antigenic determinant", as used herein, refers to that portion of a molecule that makes contact with a particular antibody (i.e., an epitope). When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

The terms "specific binding" or "specifically binding", as used herein, in reference to the interaction of an antibody and a protein or peptide, mean that the interaction is dependent upon the presence of a particular structure (i.e., the antigenic determinant or epitope) on the protein; in other words, the antibody is recognizing and binding to a specific protein structure rather than to proteins in general. For example, if an antibody is specific for epitope "A", the presence of a protein containing epitope A (or free, unlabeled A) in a reaction containing labeled "A" and the antibody will reduce the amount of labeled A bound to the antibody.

The term "sample", as used herein, is used in its broadest sense. A biological sample suspected of containing nucleic acid encoding HGBP or fragments thereof may comprise a cell, chromosomes isolated from a cell (e.g., a spread of metaphase chromosomes), genomic DNA (in solution or bound to a solid support such as for Southern analysis), RNA (in solution or bound to a solid support such as for northern analysis), cDNA (in solution or bound to a solid support), an extract from cells or a tissue, and the like.

The term "correlates with expression of a polynucleotide", as used herein, indicates that the detection of the presence of ribonucleic acid that is complementary to SEQ ID NO:2 or SEQ ID NO:4 by northern analysis is indicative of the presence of mRNA encoding HGBP in a sample and thereby correlates with expression of the transcript from the polynucleotide encoding the protein.

"Alterations" in the polynucleotide of SEQ ID NO:2 or SEQ ID NO:4, as used herein, comprise any alteration in the sequence of polynucleotides encoding HGBP including deletions, insertions, and point mutations that may be detected using hybridization assays. Included within this definition is the detection of alterations to the genomic DNA sequence which encodes HGBP (e.g., by alterations in the pattern of restriction fragment length polymorphisms capable of hybridizing to SEQ ID NO:2 or SEQ ID NO:4), the inability of a selected fragment of SEQ ID NO:2 or SEQ ID NO:4 to hybridize to a sample of genomic DNA (e.g., using allele-specific oligonucleotide probes), and improper or unexpected hybridization, such as hybridization to a locus other than the normal chromosomal locus for the polynucleotide sequence encoding HGBP (e.g., using fluorescent in situ hybridization [FISH] to metaphase chromosomes spreads).

As used herein, the term "antibody" refers to intact molecules as well as fragments thereof, such as Fab, F(ab')$_2$, and Fv, which are capable of binding the epitopic determinant. Antibodies that bind HGBP polypeptides can be prepared using intact polypeptides or fragments containing small peptides of interest as the immunizing antigen. The polypeptide or peptide used to immunize an animal can be derived from translated cDNA or synthesized chemically, and can be conjugated to a carrier protein, if desired. Commonly used carriers that are chemically coupled to peptides include bovine serum albumin and thyroglobulin. The coupled peptide is then used to immunize the animal (e.g., a mouse, a rat, or a rabbit).

The term "humanized antibody", as used herein, refers to antibody molecules in which amino acids have been replaced in the non-antigen binding regions in order to more closely resemble a human antibody, while still retaining the original binding ability.

THE INVENTION

The invention is based on the discovery of novel human guanylate binding proteins (HGBP), the polynucleotides encoding HGBP, and the use of these compositions for the diagnosis, prevention, or treatment of cancer, viral infections, inflammation, or conditions associated with impaired immunity.

Nucleic acids encoding the human HGBPA of the present invention were first identified in Incyte Clone No. 456521 from the keratinocyte cDNA library (KERANOT01) through a computer-generated search for amino acid sequence alignments. A consensus sequence, SEQ ID NO:2, was derived from the following overlapping and/or extended nucleic acid sequences: Incyte Clones 456521 (KERANOT01), 343442 (THYMNOT02), 378812 (NEUTFMT01), 394137 (TMLR2DT01), 472482 (MMLR1DT01), 521139 (MMLR2DT01), 558983 (MPHGLPT02), 568275 (MMLR3DT01), 637322 (NEUTGMT01), 794579 (OVARNOT03), 1212723 (BRSTTUT01), and 1448390 (PLACNOT02).

Figure 7:
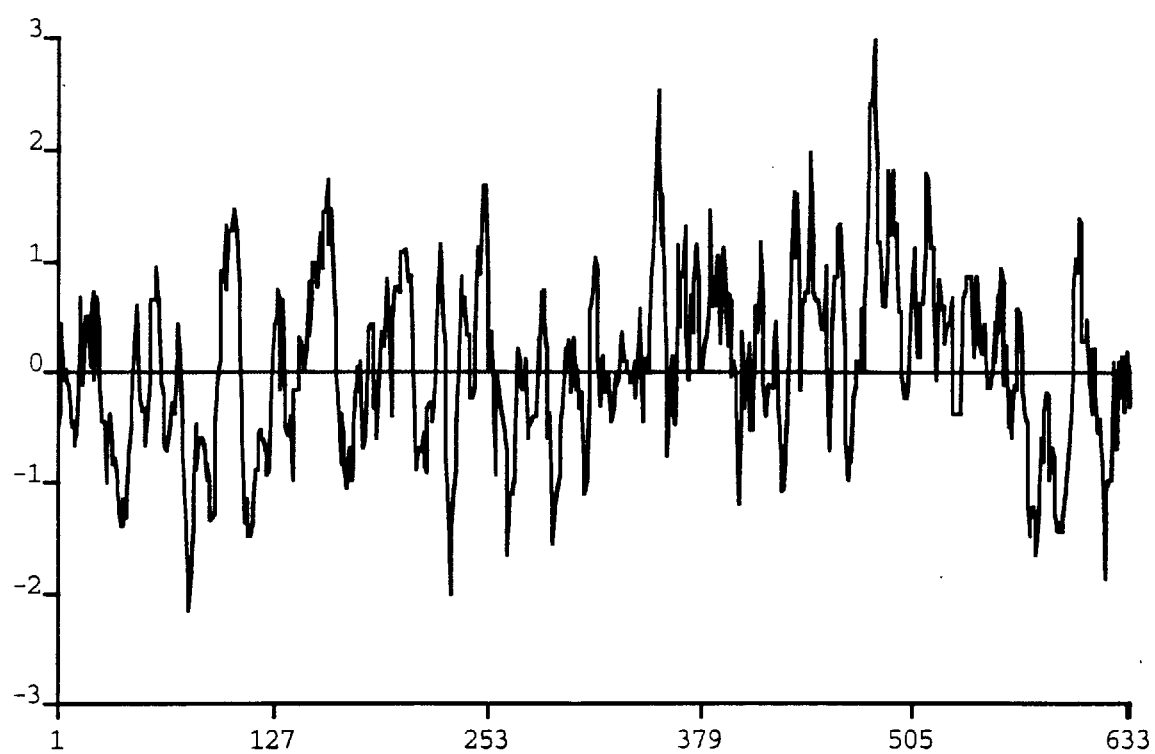
FIG. 7 shows the hydrophobicity plot for HGBPB, SEQ ID NO:3.

In one embodiment, the invention encompasses HGBPA, a polypeptide comprising the amino acid sequence of SEQ ID NO:1, as shown in FIGS. 1A, 1B, and 1C. HGBPA is 608 amino acids in length and has three potential N-glycosylation sites at $N_{111}$, $N_{155}$, and $N_{160}$. HGBPA has chemical and structural homology with human GBP-2 (GI 829177; SEQ ID NO:5). In particular, HGBPA and human GBP-2 share 90% identity. Like human GBP-1 and GBP-2, HGBPA has two of three conserved guanylate binding motifs GXXXXGKS, which starts at amino acid residue 45, and DXXG, which starts at residue 97 (FIGS. 5A and 5B). HGBPA does not have a CaaX motif at its terminus, and thus may not be prenylated. As illustrated by FIGS. 6 and 7, HGBPA and human GBP-2 have rather similar hydrophobicity plots. Northern analysis (FIG. 3) reveals that HGBPA is most abundantly expressed in cells that mediate immune responses, such as lymphocytes and macrophages.

Nucleic acids encoding the human HGBPB of the present invention were first identified in Incyte Clone No. 633446 from the neutrophil cDNA library (NEUTGMT01) through a computer-generated search for amino acid sequence alignments. A consensus sequence, SEQ ID NO:4, was derived from the following overlapping and/or extended nucleic acid sequences: Incyte Clones 633446 (NEUTGMT01), 290018 (TMLR3DT01), 338604 (NEUTFMT01), 343442 (THYMNOT02), 470941 (MMLR1DT01), 476117 (MMLR2DT01), 504780 (TMLR3DT02), and 792141 (PROSTUT03).

Figure 8:
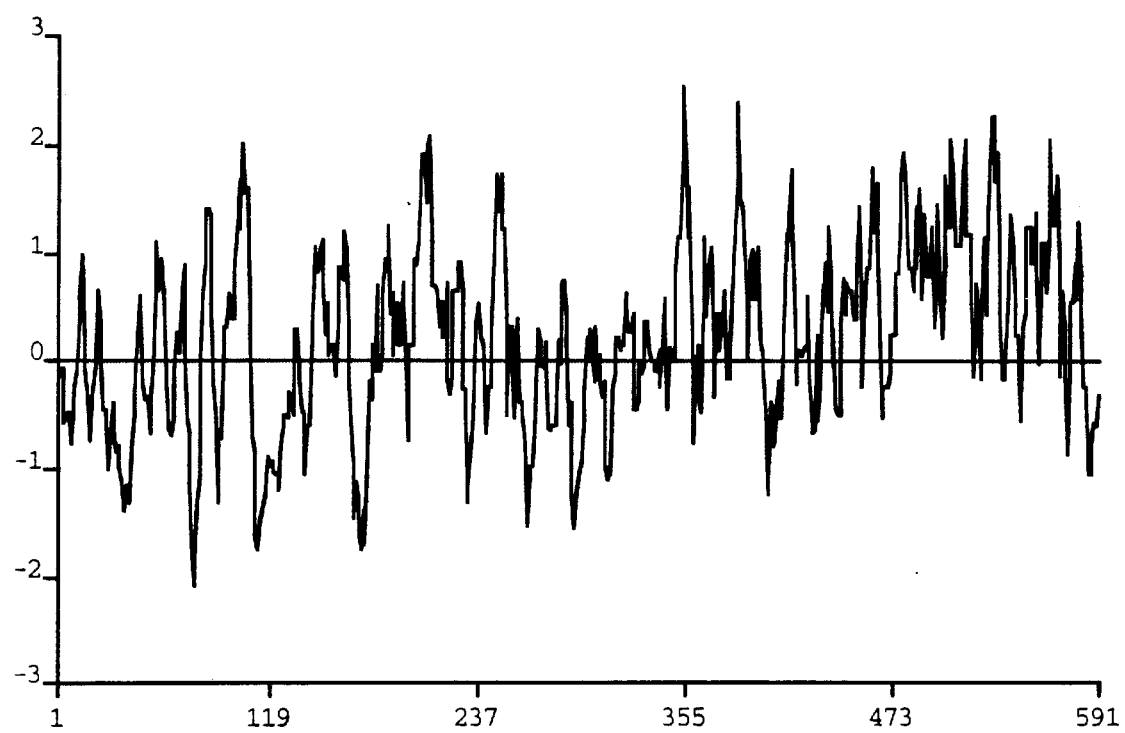
FIG. 8 shows the hydrophobicity plot for GBP-2, SEQ ID NO:5.

In one embodiment, the invention encompasses HGBPB, a polypeptide comprising the amino acid sequence of SEQ ID NO:3, as shown in FIGS. 2A, 2B, 2C and 2D. HGBPB is 633 amino acids in length and has three potential N-glycosylation sites at $N_{90}$, $N_{142}$, $N_{216}$. HGBPB has chemical and structural homology with human GBP-2 (GI 829177; SEQ ID NO:6). In particular, HGBPB and human GBP-2 share 66% identity. HGBPB has one of two guanylate binding motifs conserved in human GBP-1 and GBP-2 GXXXXGKS, which starts at amino acid residue 45 (FIG. 5). HGBPB does not have a CaaX motif at its terminus, and thus may not be prenylated. As illustrated by FIGS. 7 and 8, HGBPB and human GBP-2 have rather similar hydrophobicity plots. Northern analysis (FIG. 4) reveals that HGPB is most abundantly expressed in cells that mediate immune responses, such as lymphocytes and macrophages.

The invention also encompasses HGBP variants. A preferred HGBP variant is one having at least 80%, and more preferably 90%, amino acid sequence similarity to the HGBP amino acid sequence (SEQ ID NO:1 or SEQ ID NO:3). A most preferred HGBP variant is one having at least 95% amino acid sequence similarity to SEQ ID NO:1 or SEQ ID NO:3.

The invention also encompasses polynucleotides which encode HGBP. Accordingly, any nucleic acid sequence which encodes the amino acid sequence of HGBP can be used to generate recombinant molecules which express HGBP. In a particular embodiment, the invention encompasses the polynucleotide comprising the nucleic acid of SEQ ID NO:2 or SEQ ID NO:4 as shown in FIGS. 1A, 1B, and 1C.

It will be appreciated by those skilled in the art that as a result of the degeneracy of the genetic code, a multitude of nucleotide sequences encoding HGBP, some bearing minimal homology to the nucleotide sequences of any known and naturally occurring gene, may be produced. Thus, the invention contemplates each and every possible variation of nucleotide sequence that could be made by selecting combinations based on possible codon choices. These combinations are made in accordance with the standard triplet genetic code as applied to the nucleotide sequence of naturally occurring HGBP, and all such variations are to be considered as being specifically disclosed.

Although nucleotide sequences which encode HGBP and its variants are preferably capable of hybridizing to the nucleotide sequence of the naturally occurring HGBP under appropriately selected conditions of stringency, it may be advantageous to produce nucleotide sequences encoding HGBP or its derivatives possessing a substantially different codon usage. Codons may be selected to increase the rate at which expression of the peptide occurs in a particular prokaryotic or eukaryotic expression host in accordance with the frequency with which particular codons are utilized by the host. Other reasons for substantially altering the nucleotide sequence encoding HGBP and its derivatives without altering the encoded amino acid sequences include the production of RNA transcripts having more desirable properties, such as a greater half-life, than transcripts produced from the naturally occurring sequence.

The invention also encompasses production of a DNA sequence, or portions thereof, which encode HGBP and its derivatives, entirely by synthetic chemistry. After production, the synthetic gene may be inserted into any of the many available DNA vectors and cell systems using reagents that are well known in the art at the time of the filing of this application. Moreover, synthetic chemistry may be used to introduce mutations into a sequence encoding HGBP or any portion thereof.

Also encompassed by the invention are polynucleotide sequences that are capable of hybridizing to the claimed nucleotide sequences, and in particular, those shown in SEQ ID NO:2 or SEQ ID NO:4, under various conditions of stringency. Hybridization conditions are based on the melting temperature (Tm) of the nucleic acid binding complex or probe, as taught in Berger and Kimmel (1987; Methods Enzymol. Vol. 152), and may be used at a defined stringency.

Altered nucleic acid sequences encoding HGBP which are encompassed by the invention include deletions, insertions, or substitutions of different nucleotides resulting in a polynucleotide that encodes the same or a functionally equivalent HGBP. The encoded protein may also contain deletions, insertions, or substitutions of amino acid residues which produce a silent change and result in a functionally equivalent HGBP. Deliberate amino acid substitutions may be made on the basis of similarity in polarity, charge, solubility, hydrophobicity, hydrophilicity, and/or the amphipathic nature of the residues as long as the biological activity of HGBP is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine; glycine and alanine; asparagine and glutamine; serine and threonine; phenylalanine and tyrosine.

Also included within the scope of the present invention are alleles of the gene encoding HGBP. As used herein, an "allele" or "allelic sequence" is an alternative form of the gene which may result from at least one mutation in the nucleic acid sequence. Alleles may result in altered mRNAs or polypeptides whose structure or function may or may not be altered. Any given gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

Methods for DNA sequencing which are well known and generally available in the art may be used to practice any embodiments of the invention. The methods may employ such enzymes as the Klenow fragment of DNA polymerase I, SEQUENASE (US Biochemical Corp, Cleveland, Ohio), TAQ polymerase (Perkin Elmer), thermostable T7 polymerase (Amersham, Chicago, Ill.), or combinations of recombinant polymerases and proofreading exonucleases such as the ELONGASE amplification system marketed by Gibco BRL (Gaithersburg, Md.). Preferably, the process is automated with machines such as the Hamilton MICROLAB 2200 (Hamilton, Reno, Nev.), Peltier thermal cycler (PTC200; MJ Research, Watertown, Mass.) and the ABI 377 DNA sequencers (Perkin Elmer).

The polynucleotide sequence encoding HGBP may be extended utilizing a partial nucleotide sequence and employing various methods known in the art to detect upstream sequences such as promoters and regulatory elements. For example, one method which may be employed, "restriction-site" PCR, uses universal primers to retrieve unknown sequence adjacent to a known locus (Gobinda et al. (1993) PCR Methods Applic. 2:318–322). In particular, genomic DNA is first amplified in the presence of primer to linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region (Triglia, T. et al. (1988) Nucleic Acids Res. 16:8186). The primers may be designed using OLIGO primer analysis software (National Biosciences Inc., Plymouth, Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Another method which may be used is capture PCR which involves PCR amplification of DNA fragments adjacent to a known sequence in human and yeast artificial chromosome DNA (Lagerstrom, M. et al. (1991) PCR Methods Applic. 1:111–119). In this method, multiple restriction enzyme digestions and ligations may also be used to place an engineered double-stranded sequence into an unknown portion of the DNA molecule before performing PCR.

Another method which may be used to retrieve unknown sequences is that of Parker, J. D. et al. (1991; Nucleic Acids Res. 19:3055–3060). Additionally, one may use PCR, nested primers, and PROMOTERFINDER libraries to walk in genomic DNA (Clontech, Palo Alto, Calif.). This process avoids the need to screen libraries and may be is useful in finding intron/exon junctions.

When screening for full-length cDNAs, it is preferable to use libraries that have been size-selected to include larger cDNAs. Also, random-primed libraries are preferable in that they will contain more sequences which contain the 5' regions of genes. Use of a randomly primed library may be especially preferable for situations in which an oligo d(T) library does not yield a full-length cDNA. Genomic libraries may be useful for extension of sequence into the 5' and 3' non-translated regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and detection of the emitted wavelengths by a charge coupled device camera. Output/light intensity may be converted to electrical signal using appropriate software (e.g. GENOTYPER and SEQUENCE NAVIGATOR, Perkin Elmer) and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode HGBP, or fusion proteins or finctional equivalents thereof, may be used in recombinant DNA molecules to direct expression of HGBP in appropriate host cells. Due to the inherent degeneracy of the genetic code, other DNA sequences which encode substantially the same or a functionally equivalent amino acid sequence may be produced and these sequences may be used to clone and express HGBP.

As will be understood by those of skill in the art, it may be advantageous to produce HGBP-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence.

The nucleotide sequences of the present invention can be engineered using methods generally known in the art in order to alter the HGBP coding sequence for a variety of reasons, including but not limited to, alterations which modify the cloning, processing, and/or expression of the gene product. DNA shuffling by random fragmentation and PCR reassembly of gene fragments and synthetic oligonucleotides may be used to engineer the nucleotide sequence. For example, site-directed mutagenesis may be used to insert new restriction sites, alter glycosylation patterns, to change codon preference, to produce splice variants, or other mutations, and so forth.

In another embodiment of the invention, a natural, modified, or recombinant polynucleotide encoding HGBP may be ligated to a heterologous sequence to encode a fusion protein. For example, to screen peptide libraries for inhibitors of HGBP activity, it may be useful to encode a chimeric HGBP protein that can be recognized by a commercially available antibody. A fusion protein may also be engineered to contain a cleavage site located between a HGBP encoding sequence and the heterologous protein sequence, so that HGBP may be cleaved and purified away from the heterologous moiety.

In another embodiment, the coding sequence of HGBP may be synthesized, in whole or in part, using chemical methods well known in the art (see Caruthers, M. H. et al. (1980) Nucl. Acids Res. Symp. Ser. 215–223, Horn, T. et al. (1980) Nucl. Acids Res. Symp. Ser. 225–232). Alternatively, the protein itself may be produced using chemical methods to synthesize the HGBP amino acid sequence, or a portion thereof. For example, peptide synthesis can be performed using various solid-phase techniques (Roberge, J. Y. et al. (1995) Science 269:202–204) and automated synthesis may be achieved, for example, using the ABI 431A peptide synthesizer (Perkin Elmer).

The newly synthesized peptide may be substantially purified by preparative high performance liquid chromatography (e.g., Creighton, T. (1983) *Proteins, Structures and Molecular Principles*, WH Freeman and Co., New York, N.Y.). The composition of the synthetic peptides may be confirmed by amino acid analysis or sequencing (e.g., the Edman degradation procedure; Creighton, supra). Additionally, the amino acid sequence of HGBP, or any part thereof, may be altered during direct synthesis and/or combined using chemical methods with sequences from other proteins, or any part thereof, to produce a variant polypeptide.

In order to express a biologically active HGBP, the nucleotide sequence encoding HGBP or functional equivalents, may be inserted into an appropriate expression vector, i.e., a vector which contains the necessary elements for the transcription and translation of the inserted coding sequence.

Methods which are well known to those skilled in the art may be used to construct expression vectors containing a HGBP coding sequence and appropriate transcriptional and translational control elements. These methods include in vitro recombinant DNA techniques, synthetic techniques, and in vivo genetic recombination. Such techniques are described in Sambrook, J. et al. (1989) *Molecular Cloning, A Laboratory Manual*, Cold Spring Harbor Press, Plainview, N.Y., and Ausubel, F. M. et al. (1989) *Current Protocols in Molecular Biology*, John Wiley & Sons, New York, N.Y.

A variety of expression vector/host systems may be utilized to contain and express a HGBP coding sequence. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems.

The "control elements" or "regulatory sequences" are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the BLUESCRIPT phagemid (Stratagene, LaJolla, Calif.) or PSPORT1 plasmid (Gibco BRL) and ptrp-lac hybrids, and the like may be used. The baculovirus polyhedrin promoter may be used in insect cells. Promoters or enhancers derived from the genomes of plant cells (e.g., heat shock, RUBISCO; and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding HGBP, vectors based on SV40 or EBV may be used with an appropriate selectable marker.

In bacterial systems, a number of expression vectors. may be selected depending upon the use intended for HGBP. For example, when large quantities of HGBP are needed for the induction of antibodies, vectors which direct high level expression of fusion proteins that are readily purified may be used. Such vectors include, but are not limited to, the multifunctional *E. coli* cloning and expression vectors such as BLUESCRIPT (Stratagene), in which the sequence encoding HGBP may be ligated into the vector in frame with sequences for the amino-terminal Met and the subsequent 7 residues of β-galactosidase so that a hybrid protein is produced; pIN vectors (Van Heeke, G. and S. M. Schuster (1989) J. Biol. Chem. 264:5503–5509); and the like. pGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomvces cerevisiae*, a number of vectors containing constitutive or inducible promoters such as alpha factor, alcohol oxidase, and PGH may be used. For reviews, see Ausubel et al. (supra) and Grant et al. (1987) Methods Enzymol. 153:516–544.

In cases where plant expression vectors are used, the expression of a sequence encoding HGBP may be driven by any of a number of promoters. For example, viral promoters such as the 35S and 19S promoters of CaMV may be used alone or in combination with the omega leader sequence from TMV (Takamatsu et al. (1987) EMBO J. 6:307–311; Brisson et al. (1984) Nature 310:511–514). Alternatively, plant promoters such as the small subunit of RUBISCO or heat shock promoters may be used (Coruzzi et al. (1984) EMBO J. 3:1671–1680; Broglie et al. (1984) Science 224:838–843; Winter, J. et al. (1991) Results Probl. Cell Differ. 17:85–105). These constructs can be introduced into plant cells by direct DNA transformation or pathogen-mediated transfection. Such techniques are described in a number of generally available reviews (see, for example, Hobbs, S. or Murry, L. E. in McGraw Hill *Yearbook of Science and Technology* (1992) McGraw Hill, New York, N.Y.; pp. 191–196 or Weissbach and Weissbach (1988) *Methods for Plant Molecular Biology*, Academic Press, New York, N.Y.; pp. 421–463).

An insect system may also be used to express HGBP. For example, in one such system, *Autographa californica* nuclear polyhedrosis virus (AcNPV) is used as a vector to express foreign genes in *Spodoptera frugiperda* cells or in Trichoplusia larvae. The sequence encoding HGBP may be cloned into a non-essential region of the virus, such as the polyhedrin gene, and placed under control of the polyhedrin promoter. Successful insertion of HGBP will render the polyhedrin gene inactive and produce recombinant virus lacking coat protein. The recombinant viruses may then be used to infect, for example, *S. frugiperda* cells or Trichoplusia larvae in which HGBP may be expressed (Smith et al. (1983) J. Virol 46:584; Engelhard, E. K. et al. (1994) Proc. Nat. Acad. Sci. 91:3224–3227).

In mammalian host cells, a number of viral-based expression systems may be utilized. In cases where an adenovirus is used as an expression vector, a sequence encoding HGBP may be ligated into an adenovirus transcription/translation complex consisting of the late promoter and tripartite leader sequence. Insertion in a non-essential E1 or E3 region of the viral genome may be used to obtain a viable virus which is capable of expressing HGBP in infected host cells (Logan and Shenk (1984) Proc. Natl. Acad. Sci. 81:3655–3659). In addition, transcription enhancers, such as the Rous sarcoma virus (RSV) enhancer, may be used to increase expression in mammalian host cells.

Specific initiation signals may also be used to achieve more efficient translation of a sequence encoding HGBP. Such signals include the ATG initiation codon and adjacent sequences. In cases where sequences encoding HGBP, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf D et al. (1994) Results Probl. Cell Differ. 20:125–162; Bittner et al. (1987) Methods Enzymol. 153:516–544).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells such as CHO, HeLa, MDCK, HEK293, and WI38, which have specific cellular machinery and characteristic mechanisms for such post-translational activities, may be chosen to ensure the correct modification and processing of the foreign protein.

For long-term, high-yield production of recombinant proteins, stable expression is preferred. For example, cell lines which stably express HGBP may be transformed using expression vectors which may contain viral origins of replication and/or endogenous expression elements and a selectable marker gene on the same or separate vector. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) Cell 11:223–32) and adenine phosphoribosyltransferase (Lowy, I. et al. (1980) Cell 22:817–23) genes which can be employed in tk⁻ or aprt⁻ cells, respectively. Also, antimetabolite, antibiotic or herbicide resistance can be used as the basis for selection; for example, dhfr which confers resistance to methotrexate (Wigler, M. et al. (1980) Proc. Natl. Acad. Sci. 77:3567–70); npt, which confers resistance to the aminoglycosides neomycin and G-418 (Colbere-Garapin, F. et al. (1981) J. Mol. Biol. 150:1–14) and als or pat, which confer resistance to chlorsulfiron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) Proc. Natl. Acad. Sci. 85:8047–51). Recently, the use of visible markers has gained popularity with such markers as anthocyanins, β glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) Methods Mol. Biol. 55:121–131).

Although the presence/absence of marker gene expression suggests that the gene of interest is also present, its presence and expression may need to be confirmed. For example, if the sequence encoding HGBP is inserted within a marker gene sequence, recombinant cells containing sequences encoding HGBP can be identified by the absence of marker gene function. Alternatively, a marker gene can be placed in tandem with a sequence encoding HGBP under the control of a single promoter. Expression of the marker gene in response to induction or selection usually indicates expression of the tandem gene as well.

Alternatively, host cells which contain the coding sequence for HGBP and express HGBP may be identified by a variety of procedures known to those of skill in the art. These procedures include, but are not limited to, DNA—DNA or DNA-RNA hybridizations and protein bioassay or imununoassay techniques which include membrane, solution, or chip based technologies for the detection and/or quantification of the nucleic acid or protein.

The presence of the polynucleotide sequence encoding HGBP can be detected by DNA—DNA or DNA-RNA hybridization or amplification using probes or portions or fragments of polynucleotides encoding HGBP. Nucleic acid amplification based assays involve the use of oligonucleotides or oligomers based on the HGBP-encoding sequence to detect transformants containing DNA or RNA encoding HGBP. As used herein, "oligonucleotides" or "oligomers" refer to a nucleic acid sequence of at least about 10 nucleotides and as many as about 60 nucleotides, preferably about 15 to 30 nucleotides, and more preferably about 20–25 nucleotides, which can be used as a probe or amplimer.

A variety of protocols for detecting and measuring the expression of HGBP, using either polyclonal or monoclonal antibodies specific for the protein are known in the art. Examples include enzyme-linked immunosorbent assay (ELISA), radioimmunoassay (RIA), and fluorescent activated cell sorting (FACS). A two-site, monoclonal-based immunoassay utilizing monoclonal antibodies reactive to two non-interfering epitopes on HGBP is preferred, but a competitive binding assay may be employed. These and other assays are described, among other places, in Hampton et al. (1990; *Serological Methods, a Laboratory Manual*, APS Press, St Paul, Minn.) and Maddox et al. (1983) J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding HGBP include oligolabeling, nick translation, end-labeling or PCR amplification using a labeled nucleotide. Alternatively, the sequence encoding HGBP, or any portion of it, may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits (Pharmacia & Upjohn, (Kalamazoo, Mich.); Promega (Madison, Wis.); and U.S. Biochemical Corp., (Cleveland, Ohio). Suitable reporter molecules or labels, which may be used, include radionuclides, enzymes, fluorescent, chemiluminescent, or chromogenic agents as well as substrates, cofactors, inhibitors, magnetic particles, and the like.

Host cells transformed with a nucleotide sequence encoding HGBP may be cultured under conditions suitable for the expression and recovery of the protein from cell culture. The protein produced by a recombinant cell may be secreted or contained intracellularly depending on the sequence and/or the vector used. As will be understood by those of skill in the art, expression vectors containing polynucleotides which encode HGBP may be designed to contain signal sequences which direct secretion of HGBP through a prokaryotic or eukaryotic cell membrane. Other recombinant constructions may be used to join sequences encoding HGBP to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Inununex Corp., Seattle, Wash.). The inclusion of cleavable linker sequences such as those specific for Factor XA or enterokinase (Invitrogen, San Diego, Calif.) between the purification domain and HGBP may be used to facilitate purification. One such expression vector provides for expression of a fusion protein containing HGBP and a nucleic acid encoding 6 histidine residues followed by thioredoxin and an enterokinase cleavage site. The histidine residues facilitate purification on IMIAC (immobilized metal ion affinity chromatography) as described in Porath J. et al. (1992, Prot. Exp. Purif. 3: 263–281) while the enterokinase cleavage site provides a means for purifying HGBP from the fusion protein. A discussion of vectors which contain fusion proteins is provided in Kroll, D. J. et al. (1993; DNA Cell Biol. 12:441–453).

In addition to recombinant production, fragments of HGBP may be produced by direct peptide synthesis using solid-phase techniques (cf Stewart et al. (1969) *Solid-Phase Peptide Synthesis*, W.H. Freeman Co., San Francisco, Calif.; Merrifield J. (1963) J. Am. Chem. Soc. 85:2149–2154). In vitro protein synthesis may be performed using manual techniques or by automation. Automated synthesis may be achieved, for example, using Applied Biosystems 431A peptide synthesizer (Perkin Elmer). Various fragments of HGBP may be chemically synthesized separately and combined using chemical methods to produce the full length molecule

THERAPEUTICS

In another embodiment of the invention, HGBP or fragments thereof may be used for therapeutic purposes.

Based on the chemical and structural homology among HGBP (SEQ ID NO:1 or SEQ ID NO:3), other GBPs and northern analysis (FIGS. 3 and 4) which shows that HGBP expression is highest among cells which mediate immune system function, HGBP is believed to function in mediating the anti-viral, anti-inflammatory, or anti-cancer activities of IFN.

Since HGBP is preferentially expressed in cancer fighting cancer of the immune system (FIGS. 3 and 4), vectors containing the nucleic acid sequence encoding HGBP may be used to activate immune system cells. These vectors may be delivered into cells using technologies well known in the art. The altering of HGBP activity as a novel approach to cancer treatment may be especially useful in combination therapy with other, conventional chemotherapeutic agents. Such combinations of therapeutic agents having different cellular mechanisms of action often have synergystic effects allowing the use of lower effective doses of each agent and lessening side effects.

In another embodiment, antagonists which block or modulate the effect of HGBP may be used in those situations where such inhibition is therapeutically desirable. Such antagonists or inhibitors may be produced using methods which are generally known in the art, and include particularly the use of purified HGBP to produce antibodies or to screen libraries of pharmaceutical agents for those which specifically bind HGBP. For example, in one aspect, antibodies which are specific for HGBP may be used directly as an antagonist, or indirectly as a targeting or delivery mechanism for bringing a pharmaceutical agent to cells or tissue which express HGBP.

The antibodies may be generated using methods that are well known in the art. Such antibodies may include, but are not limited to, polyclonal, monoclonal, chimeric, single chain, Fab fragments, and fragments produced by a Fab expression library. Neutralizing antibodies, (i.e., those which inhibit dimer formation) are especially preferred for therapeutic use.

For the production of antibodies, various hosts including goats, rabbits, rats, mice, humans, and others, may be immunized by injection with HGBP or any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium parvum* are especially preferable.

It is preferred that the peptides, fragments, or oligopeptides used to induce antibodies to HGBP have an amino acid sequence consisting of at least five amino acids, and more preferably at least 10 amino acids. It is also preferable that they are identical to a portion of the amino acid sequence of the natural protein, and they may contain the entire amino acid sequence of a small, naturally occurring molecule. Short stretches of HGBP amino acids may be fused with those of another protein such as keyhole limpet hemocyanin and antibody produced against the chimeric molecule.

Monoclonal antibodies to HGBP may be prepared using any technique which provides for the production of antibody molecules by continuous cell lines in culture. These include, but are not limited to, the hybridoma technique, the human B-cell hybridoma technique, and the EBV-hybridoma technique (Koehler et al. (1975) Nature 256:495–497; Kosbor et al. (1983) Immunol. Today 4:72; Cote et al. (1983) Proc. Natl. Acad. Sci. 80:2026–2030; Cole et al. (1985) *Monoclonal Antibodies and Cancer Therapy*, Alan R. Liss Inc., New York, N.Y., pp. 77–96).

In addition, techniques developed for the production of "chimeric antibodies", the splicing of mouse antibody genes to human antibody genes to obtain a molecule with appropriate antigen specificity and biological activity can be used (Morrison et al. (1984) Proc. Natl. Acad. Sci. 81:6851–6855; Neuberger et al. (1984) Nature 312:604–608; Takeda et al. (1985) Nature 314:452–454). Alternatively, techniques described for the production of single chain antibodies may be adapted, using methods known in the art, to produce HGBP-specific single chain antibodies. Antibodies with related specificity, but of distinct idiotypic composition, may be generated by chain shuffling from random combinatorial immunoglobulin libraries (Burton D. R. (1991) Proc. Natl. Acad. Sci. 88:11120–3).

Antibodies may also be produced by inducing in vivo production in the lymphocyte population or by screening recombinant immunoglobulin libraries or panels of highly specific binding reagents as disclosed in the literature (Orlandi, et al. (1989) Proc. Natl. Acad. Sci. 86: 3833–3837; Winter, G. et al. (1991) Nature 349:293–299).

Antibody fragments which contain specific binding sites for HGBP may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse et al. (1989) Science 256:1275–1281).

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between HGBP and its specific antibody. A two-site, monoclonal-based inununoassay utilizing monoclonal antibodies reactive to two non-interfering HGBP epitopes is preferred, but a competitive binding assay may also be employed (Maddox, supra).

In another embodiment of the invention, the polynucleotides encoding HGBP, or any fragment thereof, or antisense sequences, may be used for therapeutic purposes. In one aspect, antisense to the polynucleotide encoding HGBP may be used in situations in which it would be desirable to block the synthesis of the protein. In particular, cells may be transformed with sequences complementary to polynucleotides encoding HGBP. Thus, antisense sequences may be used to modulate HGBP activity, or to achieve regulation of gene function. Such technology is now well known in the art, and sense or antisense oligomers or larger fragments, can be designed from various locations along the coding or control regions of sequences encoding HGBP.

Expression vectors derived from retroviruses, adenovirus, herpes or vaccinia viruses, or from various bacterial plasmids may be used for delivery of nucleotide sequences to the targeted organ, tissue or cell population. Methods which are well known to those skilled in the art can be used to construct recombinant vectors which will express antisense polynucleotides of the gene encoding HGBP. These techniques are described both in Sambrook et al. (supra) and in Ausubel et al. (supra).

Genes encoding HGBP can be turned off by transforming a cell or tissue with expression vectors which express high levels of a polynucleotide or fragment thereof which encodes HGBP. Such constructs may be used to introduce untranslatable sense or antisense sequences into a cell. Even in the absence of integration into the DNA, such vectors may continue to transcribe RNA molecules until all copies are disabled by endogenous nucleases. Transient expression may last for a month or more with a non-replicating vector and even longer if appropriate replication elements are part of the vector system.

As mentioned above, modifications of gene expression can be obtained by designing antisense molecules, DNA, RNA, or PNA, to the control regions of the gene encoding HGBP, i.e., the promoters, enhancers, and introns. Oligonucleotides derived from the transcription initiation site, e.g., between positions −10 and +10 from the ATG start site, are preferred.

Similarly, inhibition can be achieved using "triple helix" base-pairing methodology. Triple helix pairing is useful because it causes inhibition of the ability of the double helix to open sufficiently for the binding of polymerases, transcription factors, or regulatory molecules.

Recent therapeutic advances using triplex DNA have been described in the literature (Gee, J. E. et al. (1994) In: Huber, B. E. and B. I. Carr, *Molecular and Immunologic Approaches*, Futura Publishing Co., Mt. Kisco, N.Y.). The antisense molecules may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. Examples which may be used include engineered hammerhead motif ribozyme molecules that can specifically and efficiently catalyze endonucleolytic cleavage of sequences encoding HGBP.

Specific ribozyme cleavage sites within any potential RNA target are initially identified by scanning the target molecule for ribozyme cleavage sites which include the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Antisense molecules and ribozymes of the invention may be prepared by any method known in the art for the synthesis of RNA molecules. These include techniques for chemically synthesizing oligonucleotides such as solid phase phosphoramidite chemical synthesis. Alternatively, RNA molecules may be generated by in vitro and in vivo transcription of DNA sequences encoding HGBP. Such DNA sequences may be incorporated into a wide variety of vectors with suitable RNA polymerase promoters such as T7 or SP6. Alternatively, these cDNA constructs that synthesize antisense RNA constitutively or inducibly can be introduced into cell lines, cells, or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection and by liposome injections may be achieved using methods which are well known in the art.

Any of the therapeutic methods described above may be applied to any suitable subject including, for example, mammals such as dogs, cats, cows, horses, rabbits, monkeys, and most preferably, humans.

An additional embodiment of the invention relates to the administration of a pharmaceutical composition, in conjunction with a pharmaceutically acceptable carrier, for any of the therapeutic effects discussed above. Such pharmaceutical compositions may consist of HGBP, antibodies to HGBP, mimetics, agonists, antagonists, or inhibitors of HGBP. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a patient alone, or in combination with other agents, drugs or hormones.

The pharmaceutical compositions utilized in this invention may be administered by any number of routes including, but not limited to, oral, intravenous, intramuscular, intraarterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethylcellulose, or sodium carboxymethylcellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, succinic acids, etc. Salts tend to be more soluble in aqueous or other protonic solvents than are the corresponding free base forms. In other cases, the preferred preparation may be a lyophilized powder which may contain any or all of the following: 1–50 mM histidine, 0.1%–2% sucrose, and 2–7% mannitol, at a pH range of 4.5 to 5.5, that is combined with buffer prior to use.

After pharmaceutical compositions have been prepared, they can be placed in an appropriate container and labeled for treatment of an indicated condition. For administration of HGBP, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells, or in animal models, usually mice, rabbits, dogs, or pigs. The animal model may also be used to determine the appropriate concentration range and route of administration. Such information can then be used to determine useful doses and routes for administration in humans.

A therapeutically effective dose refers to that amount of active ingredient, for example HGBP or fragments thereof, antibodies of HGBP, agonists, antagonists or inhibitors of HGBP, which ameliorates the symptoms or condition. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio of toxic to therapeutic effects is the therapeutic index, and it can be expressed as the ratio LD50/ED50. Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

DIAGNOSTICS

In another embodiment, antibodies which specifically bind HGBP may be used for the diagnosis of conditions or diseases characterized by expression of HGBP, or in assays to monitor patients being treated with HGBP, agonists, antagonists or inhibitors. The antibodies useful for diagnostic purposes may be prepared in the same manner as those described above for therapeutics. Diagnostic assays for HGBP include methods which utilize the antibody and a label to detect HGBP in human body fluids or extracts of cells or tissues. The antibodies may be used with or without modification, and may be labeled by joining them, either covalently or non-covalently, with a reporter molecule. A wide variety of reporter molecules which are known in the art may be used, several of which are described above.

A variety of protocols including ELISA, RIA, and FACS for measuring HGBP are known in the art and provide a basis for diagnosing altered or abnormal levels of HGBP expression. Normal or standard values for HGBP expression are established by combining body fluids or cell extracts taken from normal mammalian subjects, preferably human, with antibody to HGBP under conditions suitable for complex formation. The amount of standard complex formation may be quantified by various methods, preferably by photometric means. Quantities of HGBP expressed in subject, samples from biopsied tissues are compared with the standard values. Deviation between standard and subject values establishes the parameters for diagnosing disease.

In another embodiment of the invention, the polynucleotides encoding HGBP may be used for diagnostic purposes. The polynucleotides which may be used include oligonucleotide sequences, antisense RNA and DNA molecules, and PNAs. The polynucleotides may be used to detect and quantitate gene expression in biopsied tissues in which expression of HGBP may be correlated with disease. The diagnostic assay may be used to distinguish between absence, presence, and excess expression of HGBP, and to monitor regulation of HGBP levels during therapeutic intervention.

In one aspect, hybridization with PCR probes which are capable of detecting polynucleotide sequences, including genomic sequences, encoding HGBP or closely related molecules, may be used to identify nucleic acid sequences which encode HGBP. The specificity of the probe, whether it is made from a highly specific region, e.g., 10 unique nucleotides in the 5' regulatory region, or a less specific region, e.g., especially in the 3' coding region, and the stringency of the hybridization or amplification (maximal, high, intermediate, or low) will determine whether the probe identifies only naturally occurring sequences encoding HGBP, alleles, or related sequences.

Probes may also be used for the detection of related sequences, and should preferably contain at least 50% of the nucleotides from any of the HGBP encoding sequences. The hybridization probes of the subject invention may be DNA or RNA and derived from the nucleotide sequence of SEQ ID NO:2 or SEQ ID NO:3 or from genomic sequence including promoter, enhancer elements, and introns of the naturally occurring HGBP.

Means for producing specific hybridization probes for DNAs encoding HGBP include the cloning of nucleic acid sequences encoding HGBP or HGBP derivatives into vectors for the production of mRNA probes. Such vectors are known in the art, commercially available, and may be used to synthesize RNA probes in vitro by means of the addition of the appropriate RNA polymerases and the appropriate labeled nucleotides. Hybridization probes may be labeled by a variety of reporter groups, for example, radionuclides such as 32P or 35S, or enzymatic labels, such as alkaline phosphatase coupled to the probe via avidin/biotin coupling systems, and the like.

Polynucleotide sequences encoding HGBP may be used for the diagnosis of conditions or diseases which are associated with expression of HGBP. The polynucleotide sequences encoding HGBP may be used in Southern or northern analysis, dot blot, or other membrane-based technologies; in PCR technologies; or in dip stick, pin, ELISA or chip assays utilizing fluids or tissues from patient biopsies to detect altered HGBP expression. Such qualitative or quantitative methods are well known in the art.

In a particular aspect, the nucleotide sequences encoding HGBP may be useful in assays that detect activation or induction of various cancers, particularly those mentioned above. The nucleotide sequence encoding HGBP may be labeled by standard methods, and added to a fluid or tissue sample from a patient under conditions suitable for the formation of hybridization complexes. After a suitable incubation period, the sample is washed and the signal is quantitated and compared with a standard value. If the amount of signal in the biopsied or extracted sample is significantly altered from that of a comparable control sample, the nucleotide sequence has hybridized with nucleotide sequences in the sample, and the presence of altered levels of nucleotide sequences encoding HGBP in the sample indicates the presence of the associated disease. Such assays may also be used to evaluate the efficacy of a particular therapeutic treatment regimen in animal studies, in clinical trials, or in monitoring the treatment of an individual patient.

In order to provide a basis for the diagnosis of disease associated with expression of HGBP, a normal or standard profile for expression is established. This may be accomplished by combining body fluids or cell extracts taken from normal subjects, either animal or human, with a sequence, or a fragment thereof, which encodes HGBP, under conditions suitable for hybridization or amplification. Standard hybridization may be quantified by comparing the values obtained from normal subjects with those from an experiment where a known amount of a substantially purified polynucleotide is used. Standard values obtained from normal samples may be compared with values obtained from samples from patients who are symptomatic for disease. Deviation between standard and subject values is used to establish the presence of disease.

Once disease is established and a treatment protocol is initiated, hybridization assays may be repeated on a regular basis to evaluate whether the level of expression in the patient begins to approximate that which is observed in the normal patient. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides encoding HGBP may involve the use of PCR. Such oligomers may be chemically synthesized, generated enzymatically, or produced from a recombinant source. Oligomers will preferably consist of two nucleotide sequences, one with sense orientation (5'→3') and another with antisense (3'←5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Methods which may also be used to quantitate the expression of HGBP include radiolabeling or biotinylating nucleotides, coamplification of a control nucleic acid, and standard curves onto which the experimental results are interpolated (Melby, P. C. et al. (1993) J. Imnunol. Methods, 159:235–244; Duplaa, C. et al. (1993) Anal. Biochem. 212:229–236). The speed of quantitation of multiple samples may be accelerated by running the assay in an ELISA format where the oligomer of interest is presented in various dilutions and a spectrophotometric or colorimetric response gives rapid quantitation.

In another embodiment of the invention, the nucleic acid sequence which encodes HGBP may also be used to generate hybridization probes which are useful for mapping the naturally occurring genomic sequence. The sequence may be mapped to a particular chromosome or to a specific region of the chromosome using well known techniques. Such techniques include FISH, FACS, or artificial chromosome constructions, such as yeast artificial chromosomes, bacterial artificial chromosomes, bacterial PI constructions or single chromosome cDNA libraries as reviewed in Price, C. M. (1993) Blood Rev. 7:127–134, and Trask, B. J. (1991) Trends Genet. 7:149–154.

FISH (as described in Verma et al. (1988) *Human Chromosomes: A Manual of Basic Techniques*, Pergamon Press, New York, N.Y.) may be correlated with other physical chromosome mapping techniques and genetic map data. Examples of genetic map data can be found in the 1994 Genome Issue of Science (265:1981f). Correlation between the location of the gene encoding HGBP on a physical chromosomal map and a specific disease, or predisposition to a specific disease, may help delimit the region of DNA associated with that genetic disease. The nucleotide sequences of the subject invention may be used to detect differences in gene sequences between normal, carrier, or affected individuals.

In situ hybridization of chromosomal preparations and physical mapping techniques such as linkage analysis using established chromosomal markers may be used for extending genetic maps. Often the placement of a gene on the chromosome of another mammalian species, such as mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, for example, AT to 11q22–23 (Gatti et al. (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier, or affected individuals.

In another embodiment of the invention, HGBP, its catalytic or immunogenic fragments or oligopeptides thereof, can be used for screening libraries of compounds in any of a variety of drug screening techniques. The fragment employed in such screening may be free in solution, affixed to a solid support, borne on a cell surface, or located intracellularly. The formation of binding complexes, between HGBP and the agent being tested, may be measured.

Another technique for drug screening which may be used provides for high throughput screening of compounds having suitable binding affinity to the protein of interest as described in published PCT application WO84/03564. In this method, as applied to HGBP large numbers of different small test compounds are synthesized on a solid substrate, such as plastic pins or some other surface. The test compounds are reacted with HGBP, or fragments thereof, and washed. Bound HGBP is then detected by methods well known in the art. Purified HGBP can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding HGBP specifically compete with a test compound for binding HGBP. In this manner, the antibodies can be used to detect the presence of any peptide which shares one or more antigenic determinants with HGBP.

In additional embodiments, the nucleotide sequences which encode HGBP may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I cDNA Library Construction
NEUTGMT01

The NEUTGMT01 cDNA library was constructed from normal neutrophils obtained from a pool of 20 adult blood donors. Neutrophils were separated by Ficoll/Hypaque centrifugation with no further purification (Yousefi, S. (1994) Proc. Natl. Acad. Sci. 91:10868–10872; English et al. (1974) J. of Immunological Methods 5:249–252). HISTOPAQUE 1119 and HISTOPAQUE-1077 available from Sigma Diagnostics (St. Louis, Mo.) were employed to prepare the gradient. Neutrophils were then treated with 100 pM granulocyte-monocyte colony stimulating factor (GMCSF), an activator for granulocytes and monocytes for one hour. Immediately after treatment, neutrophils were lysed immediately after treatment in buffer containing guanidinium isothiocyanate. The lysate was centrifuged over a 5.7M CsCl cushion using an SW28 rotor in an L8-70M ultracentrifuge (Beckman Instruments) for 18 hours at 25,000 rpm at ambient temperature. The RNA was extracted once with acid phenol at pH 4.0, twice with phenol chloroform at pH 8.0, precipitated using 0.3M sodium acetate and 2.5 volumes of ethanol, resuspended in DEPC-treated water and DNase treated for 15 min at 37° C. The RNA was isolated using the Qiagen OLIGOTEX kit (QIAGEN Inc., Chatsworth, Calif.) and used to construct the cDNA library.

The RNA was handled according to the recommended protocols in the SUPERSCRIPT plasmid system for cDNA synthesis and plasmid cloning (Cat #18248-013; Gibco/BRL), and cDNAs were ligated into PSPORT1. The plasmid PSPORT1 was subsequently transformed into DH5α competent cells (Cat #18258-012, Gibco/BRL).

KERANOT01

The keratinocyte culture used for the library construction was derived from the leg skin of 22-week male fetus (Lot #CC2503; 2859-1) and obtained from Clonetics Corp, San Diego, Calif.) The cells were washed twice in phosphate buffered saline and lysed immediately in a buffer containing guanidinium isothiocyanate. The lysate was extracted twice with phenol chloroform and centrifuged over a CsCl cushion using an SW28 rotor and an L8-70M ultracentrifuge (Beckman Instruments). The poly A+RNA was precipitated using 0.3M sodium acetate and 2.5 volumes of ethanol, resuspended in water and DNase treated for 15 min at 37° C., and isolated using the OLIGOTEX kit (QIAGEN).

First strand cDNA synthesis was accomplished using an oligo d(T) primer/linker which also contained an XhoI restriction site. Second strand synthesis was performed using a combination of DNA polymerase I, E. coli ligase and RNase H, followed by the addition of an EcoRI adaptor to the blunt ended cDNA. The EcoRI adapted, double-stranded cDNA was then digested with XhoI restriction enzyme and fractionated to obtain sequences which exceeded 1000 bp in size. The cDNAs were inserted into the LAMBDAZAP vector system (Stratagene); then the vector which contains the PBLUESCRIPT phagemid (Stratagene) was transformed into E. coli host cells strain XL1-BLUEMRF (Stratagene).

The phagemid forms of individual cDNA clones were obtained by the in vivo excision process. Enzymes from both pBluescript and a cotransformed f1 helper phage nicked the DNA, initiated new DNA synthesis, and created the smaller, single-stranded circular phagemid molecules which contained the cDNA insert. The phagemid DNA was released, purified, and used to reinfect fresh host cells (SOLR, Stratagene). Presence of the phagemid which carries the gene for β-lactamase allowed transformed bacteria to grow on medium containing ampicillin.

II Isolation and Sequencing of cDNA Clones
NEUTGMT01

Plasmid DNA was released from the cells and purified using the Miniprep Kit (Cat#77468; Advanced Genetic Technologies Corporation, Gaithersburg, Md.). This kit consists of a 96-well block with reagents for 960 purifications. The recommended protocol was employed except for the following changes: 1) the 96 wells were each filled with only 1 ml of sterile Terrific Broth (Cat#22711, LIFE TECHNOLOGIES, Gaithersburg, Md.) with carbenicillin at 25 mg/L and glycerol at 0.4%; 2) the bacteria were cultured for 24 hours after the wells were inoculated and then lysed with 60 μl of lysis buffer; 3) a centrifugation step employing the Beckman GS-6R @2900 rpm for 5 min was performed before the contents of the block were added to the primary filter plate; and 4) the optional step of adding isopropanol to TRIS buffer was not routinely performed. After the last step in the protocol, samples were transferred to a Beckman 96-well block for storage.

KERANOT01

Plasmid DNA was released from the cells and purified using the Miniprep Kit (Catalogue #77468; Advanced Genetic Technologies Corporation, Gaithersburg, Md.). This kit consists of a 96 well block with reagents for 960 purifications. The recommended protocol was employed except for the following changes: 1) the 96 wells were each filled with only 1 ml of sterile Terrific Broth (Catalog #22711, LIFE TECHNOLOGIES™, Gaithersburg, Md.) with carbenicillin at 25 mg/L and glycerol at 0.4%; 2) the bacteria were cultured for 24 hours after the wells were inoculated and then lysed with 60 μl of lysis buffer; 3) a centrifugation step employing the Beckman GS-6R @2900 rpm for 5 min was performed before the contents of the block were added to the primary filter plate; and 4) the optional step of adding isopropanol to TRIS buffer was not routinely performed. After the last step in the protocol, samples were transferred to a Beckman 96-well block for storage.

Alternative methods of purifying plasmid DNA include the use of MAGIC MINIPREPS DNA purification system (Catalogue #A7100, Promega) or QIAWELL plasmid, QIAWELL PLUS DNA and QIAWELL ULTRAT DNA purification systems (QIAGEN).

The cDNAs were sequenced by the method of Sanger F and AR Coulson (1975; J. Mol Biol 94:441f), using a Hamilton MICROLAB 2200 (Hamilton, Reno, Nev.) in combination with four Peltier thermalcyclers (PTC200 from MJ Research, Watertown, Mass.) and Applied Biosystems 377 or 373 DNA sequencing systems (Perkin Elmer) and reading frame was determined.

III Homology Searching of cDNA Clones and Their Deduced Proteins

Each cDNA was compared to sequences in GenBank using a search algorithm developed by Applied Biosystems and incorporated into the INHERIT 670 sequence analysis system. In this algorithm, Pattern Specification Language (TRW Inc, Los Angeles, Calif.) was used to determine regions of homology. The three parameters that determine how the sequence comparisons run were window size, window offset, and error tolerance. Using a combination of these three parameters, the DNA database was searched for sequences containing regions of homology to the query sequence, and the appropriate sequences were scored with an initial value. Subsequently, these homologous regions were examined using dot matrix homology plots to distinguish regions of homology from chance matches. Smith-Waterman alignments were used to display the results of the homology search.

Peptide and protein sequence homologies were ascertained using the INHERIT 670 sequence analysis system using the methods similar to those used in DNA sequence homologies. Pattern Specification Language and parameter windows were used to search protein databases for sequences containing regions of homology which were scored with an initial value. Dot-matrix homology plots were examined to distinguish regions of significant homology from chance matches.

BLAST, which stands for Basic Local Alignment Search Tool (Altschul, S. F. (1993) J. Mol. Evol. 36:290–300; Altschul et al. (1990) J. Mol. Biol. 215:403–410), was used to search for local sequence alignments. BLAST produces alignments of both nucleotide and amino acid sequences to determine sequence similarity. Because of the local nature of the alignments, BLAST is especially useful in determining exact matches or in identifying homologs. BLAST is useful for matches which do not contain gaps. The fundamental unit of BLAST algorithm output is the High-scoring Segment Pair (HSP).

An HSP consists of two sequence fragments of arbitrary but equal lengths whose alignment is locally maximal and for which the alignment score meets or exceeds a threshold or cutoff score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output.

IV Northern Analysis

Northern analysis is a laboratory technique used to detect the presence of a transcript of a gene and involves the hybridization of a labeled nucleotide sequence to a membrane on which RNAs from a particular cell type or tissue have been bound (Sambrook et al., supra).

Analogous computer techniques using BLAST (Altschul, S. F. 1993 and 1990, supra) are used to search for identical or related molecules in nucleotide databases such as GenBank or the LIFESEQ database (Incyte Pharmaceuticals). This analysis is much faster than multiple, membrane-based hybridizations. In addition, the sensitivity of the computer search can be modified to determine whether any particular match is categorized as exact or homologous.

The basis of the search is the product score which is defined as:

$$\frac{\% \text{ sequence identity} \times \% \text{ maximum BLAST score}}{100}$$

The product score takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

The results of northern analysis are reported as a list of libraries in which the transcript encoding HGBP occurs. Abundance and percent abundance are also reported. Abundance directly reflects the number of times a particular transcript is represented in a cDNA library, and percent abundance is abundance divided by the total number of sequences examined in the cDNA library.

V Extension of HGBP-Encoding Polynucleotides to Full Length or to Recover Regulatory Sequences Full length HGBP-encoding nucleic acid sequence (SEQ ID NO:2 or SEQ ID NO:4) is used to design oligonucleotide primers for extending a partial nucleotide sequence to full length or for obtaining 5' or 3', intron or other control sequences from genomic libraries. One primer is synthesized to initiate extension in the antisense direction (XLR) and the other is synthesized to extend sequence in the sense direction (XLF). Primers are used to facilitate the extension of the known sequence "outward" generating amplicons containing new, unknown nucleotide sequence for the region of interest. The initial primers are designed from the cDNA using OLIGO 4.06 software (National Biosciences), or another appropriate program, to be 22–30 nucleotides in length, to have a GC content of 50% or more, and to anneal to the target sequence at temperatures about 68°–72° C. Any stretch of nucleotides which would result in hairpin structures and primer-primer dimerizations is avoided.

The original, selected cDNA libraries, or a human genomic library are used to extend the sequence; the latter is most useful to obtain 5' upstream regions. If more extension is necessary or desired, additional sets of primers are designed to fuirther extend the known region.

By following the instructions for the XL-PCR kit (Perkin Elmer) and thoroughly mixing the enzyme and reaction mix, high fidelity amplification is obtained. Beginning with 40 pmol of each primer and the recommended concentrations of all other components of the kit, PCR is performed using the Peltier thermal cycler (PTC200; M.J. Research, Watertown, Mass.) and the following parameters:

| | |
|---|---|
| Step 1 | 94° C. for 1 min (initial denaturation) |
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat step 4–6 for 15 additional cycles |
| Step 8 | 94° C. for 15 sec |
| Step 9 | 65° C. for 1 min |
| Step 10 | 68° C. for 7:15 min |
| Step 11 | Repeat step 8–10 for 12 cycles |
| Step 12 | 72° C. for 8 min |
| Step 13 | 4° C. (and holding) |

A 5–10 μl aliquot of the reaction mixture is analyzed by electrophoresis on a low concentration (about 0.6–0.8%) agarose mini-gel to determine which reactions were successful in extending the sequence. Bands thought to contain the largest products are selected and removed from the gel. Further purification involves using a commercial gel extraction method such as QIAQUICK (QIAGEN Inc., Chatsworth, Calif.). After recovery of the DNA, Klenow enzyme is used to trim single-stranded, nucleotide overhangs creating blunt ends which facilitate religation and cloning.

After ethanol precipitation, the products are redissolved in 13 μl of ligation buffer, 1 μl T4-DNA ligase (15 units) and 1 μl T4 polynucleotide kinase are added, and the mixture is incubated at room temperature for 2–3 hours or overnight at 16° C. Competent *E. coli* cells (in 40 μl of appropriate media) are transformed with 3 μl of ligation mixture and cultured in 80 μl of SOC medium (Sambrook et al., supra). After incubation for one hour at 37° C., the whole transformation mixture is plated on Luria Bertani (LB)-agar (Sambrook et al., supra) containing 2× Carb. The following day, several colonies are randomly picked from each plate and cultured in 150 μl of liquid LB/2× Carb medium placed in an individual well of an appropriate, commercially-available, sterile 96-well microtiter plate. The following day, 5 μl of each overnight culture is transferred into a non-sterile 96-well plate and after dilution 1:10 with water, 5 μl of each sample is transferred into a PCR array.

For PCR amplification, 18 μl of concentrated PCR reaction mix (3.3×) containing 4 units of rTth DNA polymerase, a vector primer, and one or both of the gene specific primers used for the extension reaction are added to each well. Amplification is performed using the following conditions:

| Step 1 | 94° C. for 60 sec |
| --- | --- |
| Step 2 | 94° C. for 20 sec |
| Step 3 | 55° C. for 30 sec |
| Step 4 | 72° C. for 90 sec |
| Step 5 | Repeat steps 2–4 for an additional 29 cycles |
| Step 6 | 72° C. for 180 sec |
| Step 7 | 4° C. (and holding) |

Aliquots of the PCR reactions are run on agarose gels together with molecular weight markers. The sizes of the PCR products are compared to the original partial cDNAs, and appropriate clones are selected, ligated into plasmid, and sequenced.

VI Labeling and Use of Hybridization Probes

Hybridization probes derived from SEQ ID NO:2 or SEQ ID NO:4 are employed to screen cDNAs, genomic DNAs, or mRNAs. Although the labeling of oligonucleotides, consisting of about 20 base-pairs, is specifically described, essentially the same procedure is used with larger cDNA fragments. Oligonucleotides are designed using state-of-the-art software such as OLIGO 4.06 software (National Biosciences), labeled by combining 50 pmol of each oligomer and 250 mCi of $[\gamma-^{32}P]$ adenosine triphosphate (Amersharn) and T4 polynucleotide kinase (DuPont NEN, Boston, Mass.). The labeled oligonucleotides are substantially purified with SEPHADEX G-25 superfine resin column (Pharmacia & Upjohn). A portion containing $10^7$ counts per minute of each of the sense and antisense oligonucleotides is used in a typical membrane based hybridization analysis of human genomic DNA digested with one of the following endonucleases (Ase I, Bgl II, Eco RI, Pst I, Xba 1, or Pvu II; DuPont NEN).

The DNA from each digest is fractionated on a 0.7 percent agarose gel and transferred to nylon membranes (NYTRAN PLUS, Schleicher & Schuell, Durham, N.H.). Hybridization is carried out for 16 hours at 40° C. To remove nonspecific signals, blots are sequentially washed at room temperature under increasingly stringent conditions up to 0.1x saline sodium citrate and 0.5% sodium dodecyl sulfate. After XOMAT ARTm film (Kodak, Rochester, N.Y.) is exposed to the blots, or the blots are exposed to in a Phosphoimager cassette (Molecular Dynamics, Sunnyvale, Calif.), hybridization patterns are compared visually.

VII Antisense Molecules

Antisense molecules to the HGBP-encoding sequence, or any part thereof, is used to inhibit in vivo or in vitro expression of naturally occurring HGBP. Although use of antisense oligonucleotides, comprising about 20 base-pairs, is specifically described, essentially the same procedure is used with larger cDNA fragments. An oligonucleotide based on the coding sequences of HGBP, as shown in FIG. 1, is used to inhibit expression of naturally occurring HGBP. The complementary oligonucleotide is designed from the most unique 5' sequence as shown in FIG. 1 and used either to inhibit transcription by preventing promoter binding to the upstream nontranslated sequence or translation of an HGBP-encoding transcript by preventing the ribosome from binding. Using an appropriate portion of the signal and 5' sequence of SEQ ID NO:2 or SEQ ID NO:4, an effective antisense oligonucleotide includes any 15–20 nucleotides spanning the region which translates into the signal or 5' coding sequence of the polypeptide as shown in FIG. 1.

VIII Expression of HGBP

Expression of HGBP is accomplished by subcloning the cDNAs into appropriate vectors and transforming the vectors into host cells. In this case, the cloning vector, PSPORT, previously used for the generation of the cDNA library is used to express HGBP in E. coli. Upstream of the cloning site, this vector contains a promoter for β-galactosidase, followed by sequence containing the amino-terminal Met, and the subsequent seven residues of β-galactosidase. Immediately following these eight residues is a bacteriophage promoter useful for transcription and a linker containing a number of unique restriction sites.

Induction of an isolated, transformed bacterial strain with IPTG using standard methods produces a fusion protein which consists of the first eight residues of β-galactosidase, about 5 to 15 residues of linker, and the full length protein. The signal residues direct the secretion of HGBP into the bacterial growth media which can be used directly in the following assay for activity.

IX Demonstration of HGBP Activity

HGBP's GTP binding activity can be assayed by a technique described by Brauers, A. et al. (1996, Eur. J. Biochem. 237: 833–840). Samples of 10 ug HGBP are incubated with tracer $^{35}S$ guanosine 5'-O-[γ-thio] triphosphate ($[^{35}S]$GTP [S]; 300,000 cpm/sample) in a buffer containing 20 mM $MgCl_2$, 1 mM dithiothreitol and 0.1% Triton X-100 in a total volume of 100 ml. Unlabeled GTP[S] is added and the binding is allowed to proceed at 30° C. for 1 hour. The reaction is terminated by addition of 1 ml ice-cold buffer containing 20 mM Tris, pH 8.0, 100 mM NaCl and 25 mM $MgCl_2$. The samples are filtered through nitrocellulose membranes and washed four times with 1 ml buffer. Samples are placed in scintillation cocktail and radioactivity is measured by scintillation counting.

X Production of HGBP Specific Antibodies

HGBP that is substantially purified using PAGE electrophoresis (Sambrook, supra), or other purification techniques, is used to immnunize rabbits and to produce antibodies using standard protocols. The amino acid sequence deduced from SEQ ID NO:2 or SEQ ID NO:4 is analyzed using DNASTAR software (DNASTAR Inc.) to determine regions of high immunogenicity and a corresponding oligopolypeptide is synthesized and used to raise antibodies by means known to those of skill in the art. Selection of appropriate epitopes, such as those near the C-terminus or in hydrophilic regions, is described by Ausubel et al. (supra), and others.

Typically, the oligopeptides are 15 residues in length, synthesized using an Applied Biosystems 431A peptide synthesizer using fmoc-chemistry, and coupled to keyhole limpet hemocyanin (KLH, Sigma) by reaction with M-maleimidobenzoyl-N-hydroxysuccinimide ester (MBS; Ausubel et al., supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radioiodinated, goat anti-rabbit IgG.

XI Purification of Naturally Occurring HGBP Using Specific Antibodies

Naturally occurring or recombinant HGBP is substantially purified by immunoaffinity chromatography using antibodies specific for HGBP. An immunoaffinity column is constructed by covalently coupling HGBP antibody to an activated chromatographic resin, such as CnBr-activated SEPHAROSE (Pharmacia & Upjohn). After the coupling, the resin is blocked and washed according to the manufacturer's instructions.

Media containing HGBP is passed over the immunoaffinity column, and the column is washed under conditions that allow the preferential absorbance of HGBP (e.g., high ionic strength buffers in the presence of detergent). The column is eluted under conditions that disrupt antibody/HGBP binding (eg, a buffer of pH 2–3 or a high concentration of a chaotrope, such as urea or thiocyanate ion), and HGBP is collected.

XII Identification of Molecules Which Interact with HGBP

HGBP or biologically active fragments thereof are labeled with $^{125}$I Bolton-Hunter reagent (Bolton et al. (1973) Biochem. J. 133: 529). Candidate molecules previously arrayed in the wells of a multi-well plate are incubated with the labeled HGBP, washed and any wells with labeled HGBP complex are assayed. Data obtained using different concentrations of HGBP are used to calculate values for the nurnber, affinity, and association of HGBP with the candidate molecules.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 608 amino acids
        ( B ) TYPE: amino acid
        ( C ) STRANDEDNESS: single
        ( D ) TOPOLOGY: linear ( i i ) MOLECULE TYPE: peptide ( v i i ) IMMEDIATE SOURCE:
        ( A ) LIBRARY:
        ( B ) CLONE: Consensus ( x i ) SEQUENCE DESCRIPTION: SEQ ID NO:1:

```
Met  Ala  Leu  Glu  Ile  His  Met  Ser  Asp  Pro  Met  Cys  Leu  Ile  Glu  Asn
 1              5                        10                       15

Phe  Asn  Glu  Gln  Leu  Lys  Val  Asn  Gln  Glu  Ala  Leu  Glu  Ile  Leu  Ser
              20                       25                       30

Ala  Ile  Thr  Gln  Pro  Val  Val  Val  Val  Ala  Ile  Val  Gly  Leu  Tyr  Arg
              35                       40                       45

Thr  Gly  Lys  Ser  Tyr  Leu  Met  Asn  Lys  Leu  Ala  Gly  Lys  Asn  Lys  Gly
         50                       55                  60

Phe  Ser  Val  Ala  Ser  Thr  Val  Gln  Ser  His  Thr  Lys  Gly  Ile  Trp  Xaa
65                            70                  75                       80

Trp  Cys  Val  Pro  His  Pro  Lys  Lys  Pro  Glu  His  Thr  Leu  Val  Leu  Leu
                   85                       90                       95

Asp  Thr  Glu  Gly  Leu  Gly  Asp  Ile  Glu  Lys  Gly  Asp  Asn  Glu  Asn  Asp
                  100                      105                     110

Ser  Trp  Ile  Phe  Ala  Leu  Ala  Ile  Leu  Leu  Ser  Ser  Thr  Phe  Val  Tyr
              115                      120                     125

Asn  Ser  Ile  Gly  Thr  Ile  Asn  Gln  Gln  Ala  Met  Asp  Gln  Leu  His  Tyr
         130                      135                 140

Val  Thr  Glu  Leu  Thr  Asp  Arg  Ile  Lys  Ala  Asn  Ser  Ser  Pro  Gly  Asn
145                           150                 155                     160

Asn  Ser  Val  Asp  Asp  Ser  Ala  Asp  Phe  Val  Ser  Phe  Phe  Pro  Ala  Phe
                   165                      170                     175
```

```
Val  Trp  Thr  Leu  Arg  Asp  Phe  Thr  Leu  Glu  Leu  Glu  Val  Asp  Gly  Glu
               180                      185                     190

Pro  Ile  Thr  Ala  Asp  Asp  Tyr  Leu  Glu  Leu  Ser  Leu  Lys  Leu  Arg  Lys
               195                      200                     205

Gly  Thr  Asp  Lys  Lys  Ser  Lys  Ser  Phe  Asn  Asp  Pro  Arg  Leu  Cys  Ile
          210                      215                     220

Arg  Lys  Phe  Xaa  Pro  Lys  Arg  Lys  Xaa  Phe  Val  Xaa  Asp  Trp  Pro  Xaa
225                      230                     235                      240

Xaa  Lys  Lys  Tyr  Leu  Xaa  Xaa  Leu  Glu  Gln  Leu  Lys  Glu  Glu  Glu  Leu
                    245                     250                          255

Asn  Pro  Asp  Phe  Ile  Glu  Gln  Val  Ala  Glu  Phe  Cys  Ser  Tyr  Xaa  Leu
               260                      265                     270

Ser  His  Ser  Asn  Val  Leu  Arg  Leu  Phe  Gln  Val  Ala  Leu  Gln  Val  Asn
          275                      280                     285

Gly  Pro  Arg  Leu  Glu  Ser  Leu  Val  Leu  Thr  Tyr  Val  Asn  Ala  Ile  Gly
          290                      295                     300

Ser  Gly  Asp  Leu  Pro  Cys  Met  Glu  Asn  Ala  Val  Leu  Ala  Leu  Ala  Gln
305                      310                     315                      320

Ile  Glu  Asn  Ser  Ala  Ala  Val  Xaa  Lys  Ala  Ile  Ala  His  Tyr  Glu  Gln
                    325                     330                          335

Xaa  Met  Gly  Gln  Lys  Val  Gln  Leu  Pro  Thr  Glu  Thr  Leu  Gln  Glu  Leu
               340                      345                     350

Leu  Asp  Leu  His  Arg  Asp  Ser  Glu  Arg  Glu  Ala  Ile  Glu  Val  Phe  Met
          355                      360                     365

Lys  Asn  Ser  Phe  Lys  Asp  Val  Asp  Gln  Met  Phe  Gln  Arg  Lys  Leu  Gly
          370                      375                     380

Ala  Gln  Leu  Glu  Ala  Arg  Arg  Asp  Asp  Phe  Cys  Lys  Gln  Xaa  Ser  Lys
385                      390                     395                      400

Ala  Xaa  Ser  Asp  Cys  Cys  Met  Ala  Leu  Leu  Gln  Asp  Ile  Phe  Gly  Pro
               405                      410                     415

Leu  Glu  Glu  Asp  Val  Lys  Gln  Gly  Thr  Phe  Ser  Lys  Pro  Gly  Gly  Tyr
               420                      425                     430

Arg  Leu  Phe  Thr  Gln  Lys  Leu  Gln  Glu  Leu  Lys  Asp  Lys  Tyr  Tyr  Gln
               435                      440                     445

Val  Pro  Arg  Lys  Gly  Ile  Gln  Ala  Lys  Glu  Val  Leu  Lys  Lys  Tyr  Leu
450                      455                     460

Glu  Ser  Lys  Glu  Asp  Val  Ala  Asp  Ala  Leu  Leu  Gln  Thr  Asp  Gln  Ser
465                      470                     475                      480

Leu  Ser  Glu  Lys  Glu  Lys  Ala  Ile  Glu  Val  Glu  Arg  Ile  Lys  Ala  Glu
               485                      490                     495

Ser  Ala  Glu  Ala  Ala  Lys  Lys  Met  Leu  Glu  Glu  Ile  Gln  Lys  Lys  Asn
               500                      505                     510

Glu  Glu  Met  Met  Asp  Gln  Lys  Glu  Lys  Ser  Tyr  Gln  Glu  His  Val  Lys
          515                      520                     525

Gln  Leu  Thr  Glu  Lys  Met  Glu  Arg  Asp  Arg  Ala  Gln  Leu  Met  Glu  Glu
          530                      535                     540

Gln  Glu  Lys  Thr  Leu  Thr  Ser  Lys  Leu  Gln  Glu  Gln  Ala  Arg  Ala  Leu
545                      550                     555                      560

Lys  Glu  Arg  Cys  Gln  Gly  Glu  Ser  Thr  Gln  Leu  Gln  Asn  Glu  Ile  Gln
               565                      570                     575

Lys  Leu  Gln  Lys  Thr  Leu  Lys  Lys  Thr  Lys  Arg  Tyr  Met  Xaa  Xaa
               580                      585                     590

Lys  Pro  Lys  Arg  Ile  Leu  Lys  Pro  Thr  Arg  Ser  Phe  Phe  Cys  His  Xaa
               595                      600                     605
```

( 2 ) INFORMATION FOR SEQ ID NO:2:

( i ) SEQUENCE CHARACTERISTICS:
        ( A ) LENGTH: 2038 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( A ) LIBRARY:
        ( B ) CLONE: Consensus ( x i ) SEQUENCE DESCRIPTION: SEQ ID NO:2:

```
GTAACATCCT AGACATGGCT TTAGAGATCC ACATGTCAGA CCCCATGTGC CTCATCGAGA    60
ACTTTAATGA GCAGCTGAAG GTTAATCAGG AAGCTTTGGA GATCCTGTCT GCCATTACGC   120
AACCTGTAGT TGTGGTAGCG ATTGTGGGCC TCTATCGCAC TGGCAAATCC TACCTGATGA   180
ACAAGCTGGC TGGGAAGAAC AAGGGCTTCT CTGTTGCATC TACGGTGCAG TCTCACACCA   240
AGGGAAT Y TG GATRGGTGT GTGCCTCATC CCAAGAAGCC AGAACACACC CTAGTTCTGC   300
TCGACACTGA GGGCCTGGGA GATATAGAGA AGGGTGACAA TGAGAATGAC TCCTGGATCT   360
TTGCCTTGGC CATCCTCCTG AGCAGCACCT TCGTGTACAA TAGCATAGGA ACCATCAACC   420
AGCAGGCTAT GGACCAACTT CACTATGTGA CAGAGCTGAC AGATCGAATC AAGGCAAACT   480
CCTCACCTGG TAACAATTCT GTAGACGACT CAGCTGACTT TGTGAGCTTT TTTCCAGCAT   540
TTGTGTGGAC TCTCAGAGAT TTCACCCTGG AACTGGAAGT AGATGGAGAA CCCATCACTG   600
CTGATGACTA CTTGGAGCTT TCGCTAAAGC TAAGAAAAGG TACTGATAAG AAAAGTAAAA   660
GCTTTAATGA TCCTCGGTTG TGCATCCGAA AGTTCTTNCC CAAGAGGAAG TNCTTCGTCT   720
TNGATTGGCC CGNTNCTAAG AAGTACCTTN CTNACCTAGA GCAGCTAAAG GAGGAAGAGC   780
TGAACCCTGA TTTCATAGAA CAAGTTGCAG AATTTTGTTC CTACATNCTC AGCCATTCCA   840
ATGTACTAAG ACTCTTTCAG GTGGCATTGC AGGTCAATGG GCCTCGTCTA GAGAGCCTGG   900
TGCTGACCTA CGTCAATGCC ATCGGCAGTG GGATCTACC CTGCATGGAG AACGCAGTCC   960
TGGCCTTGGC CCAGATAGAG AACTCAGC Y G CAGTGSAAAA GGCTATTGCC CACTATGAAC  1020
AG Y AGATGGG CCAGAAGGTG CAGCTGCCCA CRGAAACCCT CCAGGAGCTG CTGGACCTGC  1080
ACAGGACAG TGAGAGAGAG GCCATTGAAG TCTTCATGAA GAACTCTTTC AAGGATGTGG   1140
ACCAAATGTT CCAGAGGAAA TTAGGGGCCC AGTTGGAAGC AAGGCGAGAT GACTTTTGTA   1200
AGCAGANTTC CAAAGCATNA TCAGATTGTT GCATGGCTTT ACTTCAGGAT ATATTTGGCC   1260
CTTTAGAAGA AGATGTCAAG CAGGGAACAT TTTCTAAACC AGGGGGTTAC CGTCTCTTTA   1320
CTCAGAAGCT GCAGGAGCTG AAGGATAAGT ACTACCAGGT GCCAAGGAAG GGGATACAGG   1380
CCAAAGAGGT GCTGAAAAAA TATTTGGAGT CCAAGGAGGA TGTGGCTGAT GCACTTCTAC   1440
AGACTGATCA GTCACTCTCA GAAAAGGAAA AAGCGATTGA AGTGGAACGT ATAAAGGCTG   1500
AATCTGCAGA AGCTGCAAAG AAAATGTTGG AGGAAATACA AAAGAAGAAT GAGGAGATGA   1560
TGGACCAGAA AGAGAAGAGT TATCAGGAAC ATGTGAAACA ATTGACTGAG AAGATGGAGA   1620
GGGACAGGGC CCAGTTAATG GAAGAGCAAG AGAAGACCCT CACTAGTAAA CTTCAGGAAC   1680
AGGCCCGAGC ACTAAAGGAG AGATGCCAAG GTGAAAGTAC CCAACTTCAA AATGAGATAC   1740
AAAAGCTACA GAAGACCCTG AAAAAAAAAA CCAAGAGATA TATGTNGNAT AAGCCTAAAA   1800
GGATCCTAAA ACCAACCAGG AGCTTTTTCT GTCATNCCTA ACCCCAAGG GCNATTAACC   1860
```

```
T G G A A A A C C A   A A T T T T T T A G   G A A T T T T G G G   A A C C A A G G T G   G T C C A C T T A T   T A A T N T T G G A       1920

T T A A A T T A A A   T T T T A G G A N T   C C T T T G C C A A   T C C A T T A A A C   C A C T T T A A A A   A G G T T T T T A C       1980

C A A A G G G A A N   C C A A T G G C C A   G T T T T C A A A T   T G G G A T T C C C   A A A A A A A T C C   N A T N G G T T           2038
```

( 2 ) INFORMATION FOR SEQ ID NO:3:

( i ) SEQUENCE CHARACTERISTICS:
        ( A ) LENGTH: 633 amino acids
        ( B ) TYPE: amino acid
        ( C ) STRANDEDNESS: single
        ( D ) TOPOLOGY: linear ( i i ) MOLECULE TYPE: peptide ( v i i ) IMMEDIATE SOURCE:
        ( A ) LIBRARY:
        ( B ) CLONE: Consensus ( x i ) SEQUENCE DESCRIPTION: SEQ ID NO:3:

```
Met   Ala   Leu   Glu   Ile   His   Met   Ser   Asp   Pro   Met   Cys   Leu   Ile   Glu   Asn
 1                       5                        10                        15

Phe   Asn   Glu   Gln   Leu   Lys   Val   Asn   Gln   Glu   Ala   Leu   Glu   Ile   Leu   Ser
                   20                        25                        30

Ala   Ile   Thr   Gln   Pro   Val   Val   Val   Ala   Ile   Val   Gly   Leu   Tyr   Arg
             35                        40                        45

Thr   Gly   Lys   Ser   Tyr   Leu   Met   Asn   Lys   Leu   Ala   Gly   Lys   Asn   Lys   Gly
       50                        55                        60

Phe   Ser   Val   Ala   Ser   Thr   Val   Gln   Ser   His   Thr   Lys   Gly   Ile   Trp   Ile
 65                        70                        75                             80

Trp   Cys   Val   Pro   His   Pro   Asn   Trp   Pro   Asn   His   Thr   Leu   Phe   Cys   Leu
                         85                        90                        95

Thr   Pro   Arg   Pro   Gly   Arg   Cys   Lys   Ala   Asp   Asn   Lys   Asn   Asp   Ile   Gln
                  100                       105                       110

Ile   Phe   Ala   Leu   Ala   Leu   Leu   Leu   Ser   Ser   Thr   Xaa   Val   Tyr   Asn   Thr
                  115                       120                       125

Val   Asn   Lys   Ile   Asp   Gln   Gly   Ala   Ile   Asp   Leu   Leu   His   Asn   Val   Thr
       130                       135                       140

Glu   Leu   Thr   Asp   Leu   Leu   Lys   Ala   Arg   Asn   Ser   Pro   Asp   Leu   Asp   Arg
145                       150                       155                            160

Val   Glu   Asp   Pro   Ala   Asp   Ser   Ala   Ser   Phe   Phe   Pro   Asp   Leu   Val   Trp
                  165                       170                            175

Thr   Leu   Lys   Asp   Phe   Cys   Leu   Gly   Leu   Glu   Ile   Asp   Gly   Gln   Leu   Val
                  180                       185                       190

Thr   Pro   Asp   Glu   Tyr   Leu   Glu   Asn   Ser   Leu   Arg   Pro   Lys   Gln   Gly   Ser
                  195                       200                       205

Asp   Gln   Arg   Val   Gln   Asn   Phe   Asn   Leu   Thr   Pro   Ser   Val   Val   Tyr   Arg
       210                       215                       220

Ser   Ser   Phe   Gln   Lys   Lys   Glu   Trp   Phe   Ile   Phe   Xaa   Leu   Pro   Ala   His
225                       230                       235                            240

Gln   Lys   Lys   Leu   Ala   Gln   Leu   Glu   Thr   Leu   Pro   Asp   Asp   Glu   Leu   Glu
                         245                       250                       255

Pro   Glu   Phe   Val   Gln   Gln   Val   Thr   Glu   Phe   Cys   Ser   Tyr   Ile   Phe   Ser
                  260                       265                       270

His   Ser   Met   Thr   Lys   Thr   Leu   Pro   Gly   Gly   Met   Gln   Val   Asn   Gly   Pro
             275                       280                       285

Arg   Leu   Glu   Ser   Leu   Val   Leu   Thr   Tyr   Val   Asn   Ala   Ile   Ser   Ser   Gly
       290                       295                       300
```

-continued

| | | | | | | | | | | | | | | | |
|---|---|---|---|---|---|---|---|---|---|---|---|---|---|---|---|
| Asp | Leu | Pro | Cys | Met | Glu | Asn | Ala | Val | Leu | Ala | Leu | Ala | Gln | Arg | Glu |
| 305 | | | | 310 | | | | | 315 | | | | | | 320 |
| Asn | Ser | Ala | Ala | Val | Gln | Lys | Ala | Ile | Ala | His | Tyr | Asp | Gln | Gln | Met |
| | | | | 325 | | | | 330 | | | | | 335 | | |
| Gly | Gln | Lys | Val | Gln | Leu | Pro | Thr | Glu | Thr | Leu | Gln | Glu | Leu | Leu | Asp |
| | | | 340 | | | | | 345 | | | | | 350 | | |
| Leu | His | Arg | Asp | Ser | Glu | Arg | Glu | Ala | Ile | Glu | Val | Phe | Met | Lys | Asn |
| | | 355 | | | | | 360 | | | | | 365 | | | |
| Ser | Phe | Lys | Asp | Val | Asp | Gln | Ser | Phe | Gln | Lys | Glu | Leu | Glu | Thr | Leu |
| | 370 | | | | | 375 | | | | | 380 | | | | |
| Leu | Asp | Ala | Lys | Gln | Asn | Asp | Ile | Cys | Lys | Arg | Asn | Leu | Glu | Ala | Ser |
| 385 | | | | | 390 | | | | | 395 | | | | | 400 |
| Ser | Asp | Tyr | Cys | Ser | Ala | Leu | Leu | Lys | Asp | Ile | Phe | Gly | Pro | Leu | Glu |
| | | | | 405 | | | | | 410 | | | | | 415 | |
| Glu | Ala | Val | Lys | Gln | Gly | Ile | Tyr | Ser | Lys | Pro | Gly | Gly | His | Asn | Leu |
| | | | 420 | | | | | 425 | | | | | 430 | | |
| Phe | Ile | Gln | Lys | Thr | Glu | Glu | Leu | Lys | Ala | Lys | Tyr | Tyr | Arg | Glu | Pro |
| | | 435 | | | | | 440 | | | | | 445 | | | |
| Arg | Lys | Gly | Ile | Gln | Ala | Glu | Val | Leu | Gln | Lys | Tyr | Leu | Lys | Ser | |
| | 450 | | | | | 455 | | | | | 460 | | | | |
| Lys | Glu | Ser | Val | Ser | His | Ala | Ile | Leu | Gln | Thr | Asp | Gln | Ala | Leu | Thr |
| 465 | | | | | 470 | | | | | 475 | | | | | 480 |
| Glu | Thr | Glu | Lys | Lys | Lys | Lys | Glu | Ala | Gln | Val | Lys | Ala | Glu | Ala | Glu |
| | | | | 485 | | | | | 490 | | | | | 495 | |
| Lys | Ala | Glu | Ala | Gln | Arg | Leu | Ala | Ala | Ile | Gln | Arg | Gln | Asn | Glu | Gln |
| | | | 500 | | | | | 505 | | | | | 510 | | |
| Met | Met | Gln | Glu | Arg | Glu | Arg | Leu | His | Gln | Glu | Gln | Val | Arg | Gln | Met |
| | | 515 | | | | | 520 | | | | | 525 | | | |
| Glu | Ile | Ala | Lys | Gln | Asn | Trp | Leu | Ala | Glu | Gln | Gln | Lys | Met | Gln | Glu |
| | 530 | | | | | 535 | | | | | 540 | | | | |
| Gln | Gln | Met | Gln | Glu | Gln | Ala | Ala | Gln | Ser | Ala | Gln | His | Ser | Lys | Leu |
| 545 | | | | | 550 | | | | | 555 | | | | | 560 |
| Lys | Ile | Glu | Ala | Phe | Ser | Val | Ser | Ser | Ser | Thr | Xaa | Arg | Gly | Leu | Leu |
| | | | | 565 | | | | | 570 | | | | | 575 | |
| Ile | Thr | Met | Ile | His | Val | Phe | Tyr | Ser | Lys | Val | Leu | Asn | Met | Gly | Val |
| | | | 580 | | | | | 585 | | | | | 590 | | |
| Ser | Phe | Phe | Tyr | Ser | Leu | Ser | Leu | Met | Thr | Gln | Gln | Lys | Arg | Asn | Cys |
| | | 595 | | | | | 600 | | | | | 605 | | | |
| Arg | Pro | Trp | Asp | Asn | Gln | His | Leu | Asn | Lys | Leu | Tyr | Asn | Tyr | Phe | Phe |
| | 610 | | | | | 615 | | | | | 620 | | | | |
| Lys | Leu | Ser | Tyr | Arg | Val | Ile | Arg | Leu | | | | | | | |
| 625 | | | | | 630 | | | | | | | | | | |

( 2 ) INFORMATION FOR SEQ ID NO:4:

( i ) SEQUENCE CHARACTERISTICS:
        ( A ) LENGTH: 2381 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( A ) LIBRARY:
        ( B ) CLONE: Consensus ( x i ) SEQUENCE DESCRIPTION: SEQ ID NO:4:

-continued

```
AACTTGGTGC TGCGGGCACT TTGGGTCCAC ACTGCCTTTA TGAGCTGTAA CACTCACTGG      60
GAATGTCTGC AGCTTCACTC CTGAAGCCAG CGAGACCACG AACCCACCAG GAGGAACAAA     120
CAACTCCAGA CGCGCAGCCT TAAGAGCTGT AACACTCACC GCGAAGGTCT GCAGCTTCAC     180
TCCTGAGCCA GCCAGACCAC GAACCCACCA GAAGGAAGAA ACTCCAAACA CATCCGAACA     240
TCAGAAGTGA GCAAACTCCT GACACGCCAC CTTTAAGAAC CGTGACACTC AACGCTAGGG     300
TCCGCGGCTT CATTCTTGAA GTCAGTGAGA CCAAGAACCC ACCAATTCCG GACACGGCAA     360
AGTAACATCC TAGACATGGC TTTAGAGATC CACATGTCAG ACCCCATGTG CCTCATCGAG     420
AACTTTAATG AGCAGCTGAA GGTTAATCAG GAAGCTTTGG AGATCCTGTC TGCCATTACG     480
CAACCTGTAG TTGTGGTAGC GATTGTGGGC CTCTATCGCA CTGGCAAATC CTACCTGATG     540
AACAAGCTGG CTGGGAAGAA CAAGGGCTTC TCTGTTGCAT CTACGGTGCA GTCTCACACC     600
AAGGGAATTT GGATATGGTG TGTGCCTCAT CCCAACTGGC CAAATCACAC ATTATTCTGC     660
TTGACACCGA GGCCTGGGAG ATGTAAAGCT GACAACAAGA ATGATATCCA GATCTTTGCA     720
CTGGCACTCT TACTGAGCAG CACTTTNGTG TACAATACTG TGAACAAAAT TGATCAGGGT     780
GCTATCGACC TACTGCACAA TGTGACAGAA CTGACAGATC TGCTCAAGGC AAGAAACTCA     840
CCCGACCTTG ACAGGGTTGA AGATCCTGCT GACTCTGCGA GCTTCTTCCC AGACTTAGTG     900
TGGACTCTGA AAGATTTCTG CTTAGGCCTG GAAATAGATG GCAACTTGT CACACCAGAT      960
GAATACCTGG AGAATTCCCT AAGGCCAAAG CAAGGTAGTG ATCAAAGAGT TCAAAATTTC    1020
AATTTGACCC CGTCTGTGGT ATACAGRAGT TCTTTCCAAA AAAAGGAATG GTTTATCTTT    1080
GANTTACCTG CTCACCAAAA AAAGCTTGCC CAACTTGAAA CACTGCCTGA TGATGAGCTA    1140
GAGCCTGAAT TTGTGCAACA AGTGACAGAA TTTTGTTCCT ACATCTTTAG CCATTCAATG    1200
ACCAAGACTC TTCCAGGTGG CATGCAGGTC AATGGGCCTC GTCTAGAGAG CCTGGTGCTG    1260
ACCTACGTCA ATGCCATCAG CAGTGGGGAT CTGCCTTGCA TGGAGAACGC AGTCCTGGCC    1320
TTGGCCCAGA GAGAGAACTC AGCTGCAGTG CAAAAGGCTA TTGCCCACTA TGACCAGCAG    1380
ATGGGCCAGA AGGTGCAGCT GCCCACGGAA ACCCTCCAGG AGCTGCTGGA CCTGCACAGG    1440
GACAGTGAGA GAGAGGCCAT TGAAGTCTTC ATGAAGAACT CTTTCAAGGA TGTAGACCAA    1500
AGTTTCCAGA AAGAATTGGA GACTCTACTA GATGCAAAAC AGAATGACAT TTGTAAACGG    1560
AACCTGGAAG CATCCTCGGA TTATTGCTCG GCTTTACTTA AGGATATTTT TGGTCCTCTA    1620
GAAGAAGCAG TGAAGCAGGG AATTTATTCT AAGCCAGGAG GCCATAATCT CTTCATTCAG    1680
AAAACAGAAG AACTGAAGGC AAAGTACTAT CGGGAGCCTC GGAAAGGAAT ACAGGCTGAA    1740
GAAGTTCTGC AGAAATATTT AAAGTCCAAG GAGTCTGTGA GTCATGCAAT ATTACAGACT    1800
GACCAGGCTC TCACAGAGAC GGAAAAAAAG AAGAAAGAGG CACAAGTGAA AGCAGAAGCT    1860
GAAAAGGCTG AAGCGCAAAG GTTGGCGGCG ATTCAAAGGC AGAACGAGCA AATGATGCAG    1920
GAGAGGGAGA GACTCCATCA GGAACAAGTG AGACAAATGG AGATAGCCAA ACAAAATTGG    1980
CTGGCAGAGC AACAGAAAAT GCAGGAACAA CAGATGCAGG AACAGGCTGC ACAGTCAGCA    2040
CAACATTCCA AGCTCAAAAT AGAGGCCTTC TCAGTGAGYT CCAGCACGSC CAGAGGACTG    2100
TTAATAACGA TGATCCATGT GTTTTACTCT AAAGTGCTAA ATATGGGAGT TTCCTTTTTT    2160
TACTCTTTGT CACTGATGAC ACAACAGAAA AGAAACTGTA GACCTTGGGA CAATCAACAT    2220
TTAAATAAAC TTTATAATTA TTTTTTCAAA CTTTCATATA GAGTTATAAG GTTATGATGC    2280
TGGTATCTGG TAAAATGTAC ATCCCAGTAG TCCAATAGTT TAAATGTTTA TTGCTTCCTT    2340
TAAGNGRTTA TAAATTGTAT AAGGGACATT GTATCACTGC C                        2381
```

( 2 ) INFORMATION FOR SEQ ID NO:5:

( i ) SEQUENCE CHARACTERISTICS:
        ( A ) LENGTH: 591 amino acids
        ( B ) TYPE: amino acid
        ( C ) STRANDEDNESS: single
        ( D ) TOPOLOGY: linear ( i i ) MOLECULE TYPE: peptide ( v i i ) IMMEDIATE SOURCE:
        ( A ) LIBRARY: GenBank
        ( B ) CLONE: 829177

( x i ) SEQUENCE DESCRIPTION: SEQ ID NO:5:

```
Met Ala Pro Glu Ile Asn Leu Pro Gly Pro Met Ser Leu Ile Asp Asn
 1               5                  10                  15
Thr Lys Gly Gln Leu Val Val Asn Pro Glu Ala Leu Lys Ile Leu Ser
             20                  25                  30
Ala Ile Thr Gln Pro Val Val Val Ala Ile Val Gly Leu Tyr Arg
         35                  40                  45
Thr Gly Lys Ser Tyr Leu Met Asn Lys Leu Ala Gly Lys Lys Asn Gly
     50                  55                  60
Phe Ser Leu Gly Ser Thr Val Lys Ser His Thr Lys Gly Ile Trp Met
65                  70                  75                  80
Trp Cys Val Pro His Pro Lys Lys Pro Glu His Thr Leu Val Leu Leu
                 85                  90                  95
Asp Thr Glu Gly Leu Gly Asp Ile Glu Lys Gly Asp Asn Glu Asn Asp
                100                 105                 110
Ser Trp Ile Phe Ala Leu Ala Ile Leu Leu Ser Ser Thr Phe Val Tyr
             115                 120                 125
Asn Ser Met Gly Thr Ile Asn Gln Gln Ala Met Asp Gln Leu His Tyr
         130                 135                 140
Val Thr Glu Leu Thr Asp Arg Ile Lys Ala Asn Ser Ser Pro Gly Asn
145                 150                 155                 160
Asn Ser Val Asp Asp Ser Ala Asp Phe Val Ser Phe Phe Pro Ala Phe
                165                 170                 175
Val Trp Thr Leu Arg Asp Phe Thr Leu Glu Leu Glu Val Asp Gly Glu
             180                 185                 190
Pro Ile Thr Ala Asp Asp Tyr Leu Glu Leu Ser Leu Lys Leu Arg Lys
         195                 200                 205
Gly Thr Asp Lys Lys Ser Lys Ser Phe Asn Asp Pro Arg Leu Cys Ile
     210                 215                 220
Arg Lys Phe Phe Pro Lys Arg Lys Cys Phe Val Phe Asp Trp Pro Ala
225                 230                 235                 240
Pro Lys Lys Tyr Leu Ala His Leu Glu Gln Leu Lys Glu Glu Glu Leu
                245                 250                 255
Asn Pro Asp Phe Ile Glu Gln Val Ala Glu Phe Cys Ser Tyr Ile Leu
             260                 265                 270
Ser His Ser Asn Val Lys Thr Leu Ser Gly Gly Ile Ala Val Asn Gly
         275                 280                 285
Pro Arg Leu Glu Ser Leu Val Leu Thr Tyr Val Asn Ala Ile Ser Ser
     290                 295                 300
Gly Asp Leu Pro Cys Met Glu Asn Ala Val Leu Ala Leu Ala Gln Ile
305                 310                 315                 320
Glu Asn Ser Ala Ala Val Glu Lys Ala Ile Ala His Tyr Glu Gln Gln
                325                 330                 335
```

```
Met  Gly  Gln  Lys  Val  Gln  Leu  Pro  Thr  Glu  Thr  Leu  Gln  Glu  Leu  Leu
          340                      345                     350

Asp  Leu  His  Arg  Asp  Ser  Glu  Arg  Glu  Ala  Ile  Glu  Val  Phe  Met  Lys
          355                      360                     365

Asn  Ser  Phe  Lys  Asp  Val  Asp  Gln  Met  Phe  Gln  Arg  Lys  Leu  Gly  Ala
     370                      375                     380

Gln  Leu  Glu  Ala  Arg  Arg  Asp  Asp  Phe  Cys  Lys  Gln  Asn  Ser  Lys  Ala
385                      390                     395                      400

Ser  Ser  Asp  Cys  Cys  Met  Ala  Leu  Leu  Gln  Asp  Ile  Phe  Gly  Pro  Leu
               405                      410                     415

Glu  Glu  Asp  Val  Lys  Gln  Gly  Thr  Phe  Ser  Lys  Pro  Gly  Gly  Tyr  Arg
               420                      425                     430

Leu  Phe  Thr  Gln  Lys  Leu  Gln  Glu  Leu  Lys  Asn  Lys  Tyr  Tyr  Gln  Val
          435                      440                     445

Pro  Arg  Lys  Gly  Ile  Gln  Ala  Lys  Glu  Val  Leu  Lys  Lys  Tyr  Leu  Glu
     450                      455                     460

Ser  Lys  Glu  Asp  Val  Ala  Asp  Ala  Leu  Leu  Gln  Thr  Asp  Gln  Ser  Leu
465                      470                     475                      480

Ser  Glu  Lys  Glu  Lys  Ala  Ile  Glu  Val  Glu  Arg  Ile  Lys  Ala  Glu  Ser
               485                      490                     495

Ala  Glu  Ala  Ala  Lys  Lys  Met  Leu  Glu  Glu  Ile  Gln  Lys  Lys  Asn  Glu
               500                      505                     510

Glu  Met  Met  Gln  Gln  Lys  Glu  Lys  Ser  Tyr  Gln  Glu  His  Val  Lys  Gln
          515                      520                     525

Leu  Thr  Glu  Lys  Met  Glu  Arg  Asp  Arg  Ala  Gln  Leu  Met  Ala  Glu  Gln
          530                      535                     540

Glu  Lys  Thr  Leu  Ala  Leu  Lys  Leu  Gln  Glu  Gln  Glu  Arg  Leu  Leu  Lys
545                      550                     555                      560

Glu  Gly  Phe  Glu  Asn  Glu  Ser  Lys  Arg  Leu  Gln  Lys  Asp  Ile  Trp  Asp
               565                      570                     575

Ile  Gln  Met  Arg  Ser  Lys  Ser  Leu  Glu  Pro  Ile  Cys  Asn  Ile  Leu
          580                      585                     590
```

(2) INFORMATION FOR SEQ ID NO:6:

(i) SEQUENCE CHARACTERISTICS:
        (A) LENGTH: 592 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (A) LIBRARY: GenBank
        (B) CLONE: 183002

(xi) SEQUENCE DESCRIPTION: SEQ ID NO:6:

```
Met  Ala  Ser  Glu  Ile  His  Met  Thr  Gly  Pro  Met  Cys  Leu  Ile  Glu  Asn
1                   5                   10                      15

Thr  Asn  Gly  Arg  Leu  Met  Ala  Asn  Pro  Glu  Ala  Leu  Lys  Ile  Leu  Ser
               20                      25                      30

Ala  Ile  Thr  Gln  Pro  Met  Val  Val  Ala  Ile  Val  Gly  Leu  Tyr  Arg
          35                      40                      45

Thr  Gly  Lys  Ser  Tyr  Leu  Met  Asn  Lys  Leu  Ala  Gly  Lys  Lys  Lys  Gly
     50                      55                      60

Phe  Ser  Leu  Gly  Ser  Thr  Val  Gln  Ser  His  Thr  Lys  Gly  Ile  Trp  Met
65                       70                      75                       80
```

```
Trp  Cys  Val  Pro  His  Pro  Lys  Lys  Pro  Gly  His  Ile  Leu  Val  Leu  Leu
               85                  90                            95

Asp  Thr  Glu  Gly  Leu  Gly  Asp  Val  Glu  Lys  Gly  Asp  Asn  Gln  Asn  Asp
              100                 105                      110

Ser  Trp  Ile  Phe  Ala  Leu  Ala  Val  Leu  Leu  Ser  Ser  Thr  Phe  Val  Tyr
              115                 120                      125

Asn  Ser  Ile  Gly  Thr  Ile  Asn  Gln  Gln  Ala  Met  Asp  Gln  Leu  Tyr  Tyr
         130                 135                      140

Val  Thr  Glu  Leu  Thr  His  Arg  Ile  Arg  Ser  Lys  Ser  Ser  Pro  Asp  Glu
145                           150                 155                      160

Asn  Glu  Asn  Glu  Val  Glu  Asp  Ser  Ala  Asp  Phe  Val  Ser  Phe  Phe  Pro
                   165                      170                      175

Asp  Phe  Val  Trp  Thr  Leu  Arg  Asp  Phe  Ser  Leu  Asp  Leu  Glu  Ala  Asp
              180                      185                      190

Gly  Gln  Pro  Leu  Thr  Pro  Asp  Glu  Tyr  Leu  Thr  Tyr  Ser  Leu  Lys  Leu
              195                 200                      205

Lys  Lys  Gly  Thr  Ser  Gln  Lys  Asp  Glu  Thr  Phe  Asn  Leu  Pro  Arg  Leu
         210                 215                      220

Cys  Ile  Arg  Lys  Phe  Phe  Pro  Lys  Lys  Lys  Cys  Phe  Val  Phe  Asp  Arg
225                      230                      235                      240

Pro  Val  His  Arg  Arg  Lys  Leu  Ala  Gln  Leu  Glu  Lys  Leu  Gln  Asp  Glu
                   245                      250                      255

Glu  Leu  Asp  Pro  Glu  Phe  Val  Gln  Gln  Val  Ala  Asp  Phe  Cys  Ser  Tyr
              260                      265                      270

Ile  Phe  Ser  Asn  Ser  Lys  Thr  Lys  Thr  Leu  Ser  Gly  Gly  Ile  Gln  Val
         275                      280                 285

Asn  Gly  Pro  Arg  Leu  Glu  Ser  Leu  Val  Leu  Thr  Tyr  Val  Asn  Ala  Ile
290                           295                      300

Ser  Ser  Gly  Asp  Leu  Pro  Cys  Met  Glu  Asn  Ala  Val  Leu  Ala  Leu  Ala
305                      310                      315                      320

Gln  Ile  Glu  Asn  Ser  Ala  Ala  Val  Gln  Lys  Ala  Ile  Ala  His  Tyr  Glu
                   325                      330                      335

Gln  Gln  Met  Gly  Gln  Lys  Val  Gln  Leu  Pro  Thr  Glu  Ser  Leu  Gln  Glu
              340                      345                      350

Leu  Leu  Asp  Leu  His  Arg  Asp  Ser  Glu  Arg  Glu  Ala  Ile  Glu  Val  Phe
              355                 360                      365

Ile  Arg  Ser  Ser  Phe  Lys  Asp  Val  Asp  His  Leu  Phe  Gln  Lys  Glu  Leu
         370                 375                      380

Ala  Ala  Gln  Leu  Glu  Lys  Lys  Arg  Asp  Asp  Phe  Cys  Lys  Gln  Asn  Gln
385                      390                      395                      400

Glu  Ala  Ser  Ser  Asp  Arg  Cys  Ser  Gly  Leu  Leu  Gln  Val  Ile  Phe  Ser
                   405                      410                      415

Pro  Leu  Glu  Glu  Glu  Val  Lys  Ala  Gly  Ile  Tyr  Ser  Lys  Pro  Gly  Gly
              420                      425                      430

Tyr  Arg  Leu  Phe  Val  Gln  Lys  Leu  Gln  Asp  Leu  Lys  Lys  Lys  Tyr  Tyr
         435                      440                      445

Glu  Glu  Pro  Arg  Lys  Gly  Ile  Gln  Ala  Glu  Glu  Ile  Leu  Gln  Thr  Tyr
         450                      455                      460

Leu  Lys  Ser  Lys  Glu  Ser  Met  Thr  Asp  Ala  Ile  Leu  Gln  Thr  Asp  Gln
465                      470                      475                      480

Thr  Leu  Thr  Glu  Lys  Glu  Lys  Glu  Ile  Glu  Val  Glu  Arg  Val  Lys  Ala
                   485                      490                      495

Glu  Ser  Ala  Gln  Ala  Ser  Ala  Lys  Met  Leu  Gln  Glu  Met  Gln  Arg  Lys
              500                      505                      510
```

|   |   |   |   |   |   |   |   |   |   |   |   |   |   |   |
|---|---|---|---|---|---|---|---|---|---|---|---|---|---|---|
| Asn | Glu | Gln<br>515 | Met | Met | Glu | Gln | Lys<br>520 | Glu | Arg | Ser | Tyr | Gln<br>525 | Glu | His | Leu |
| Lys | Gln<br>530 | Leu | Thr | Glu | Lys | Met<br>535 | Glu | Asn | Asp | Arg | Val<br>540 | Gln | Leu | Leu | Lys |
| Glu<br>545 | Gln | Glu | Arg | Thr | Leu<br>550 | Ala | Leu | Lys | Leu | Gln<br>555 | Glu | Gln | Glu | Gln | Leu<br>560 |
| Leu | Lys | Glu | Gly | Phe<br>565 | Gln | Lys | Glu | Ser | Arg<br>570 | Ile | Met | Lys | Asn | Glu<br>575 | Ile |
| Gln | Asp | Leu | Gln<br>580 | Thr | Lys | Met | Arg | Arg<br>585 | Arg | Lys | Ala | Cys | Thr<br>590 | Ile | Ser |

What is claimed is:

1. An isolated polynucleotide encoding a polypeptide having the amino acid sequence of SEQ ID NO:1.

2. A hybridization probe comprising the polynucleotide of claim 1.

3. An isolated polynucleotide comprising SEQ ID NO:2.

4. An isolated polynucleotide which is fully complementary to SEQ ID NO:2.

5. A hybridization probe comprising the polynucleotide of claim 4.

6. An expression vector containing the polynucleotide of claim 1.

7. A host cell containing the expression vector of claim 6.

8. A method for producing a polypeptide comprising the amino acid sequence of SEQ ID NO:1, the method comprising the steps of:

a) culturing the host cell of claim 7 under conditions suitable for the expression of the polypeptide; and b) recovering the polypeptide from the host cell culture.

* * * * *